US008846111B2

(12) United States Patent
Lyons et al.

(10) Patent No.: US 8,846,111 B2
(45) Date of Patent: Sep. 30, 2014

(54) COMPOSITIONS AND METHODS FOR ESTABLISHING AND/OR MAINTAINING PREGNANCY

(75) Inventors: Thomas P. Lyons, Nicholasville, KY (US); Ronan Power, Lexington, KY (US)

(73) Assignee: Alltech, Inc., Nicholasville, KY (US)

( * ) Notice: Subject to any disclaimer, the term of this patent is extended or adjusted under 35 U.S.C. 154(b) by 0 days.

(21) Appl. No.: 12/122,331

(22) Filed: May 16, 2008

(65) Prior Publication Data
US 2008/0286382 A1    Nov. 20, 2008

Related U.S. Application Data

(60) Provisional application No. 60/930,752, filed on May 18, 2007.

(51) Int. Cl.
*A61K 33/04*    (2006.01)
*A61K 36/06*    (2006.01)

(52) U.S. Cl.
CPC ............... *A61K 36/06* (2013.01); *A61K 33/04* (2013.01)
USPC ........................................................ 424/702

(58) Field of Classification Search
None
See application file for complete search history.

(56) References Cited

U.S. PATENT DOCUMENTS

| | | | |
|---|---|---|---|
| 5,221,545 | A | 6/1993 | Borschel |
| 6,197,295 | B1 | 3/2001 | Hsia |
| 6,576,233 | B2 | 6/2003 | Hsia |
| 6,660,531 | B2 | 12/2003 | Stewart |
| 6,911,550 | B2 | 6/2005 | Abdel-Monem |
| 2001/0043925 | A1 | 11/2001 | Hsia |
| 2001/0053553 | A1 | 12/2001 | Stewart |
| 2004/0254239 | A1 | 12/2004 | Abdel-Monem |
| 2005/0069594 | A1 | 3/2005 | Lubinski |
| 2005/0089530 | A1 | 4/2005 | Moesgaard |
| 2006/0247172 | A1 | 11/2006 | Unemori |

FOREIGN PATENT DOCUMENTS

| | | | |
|---|---|---|---|
| CN | 1778199 A | * | 5/2006 |
| WO | WO 91/02251 A1 | * | 2/1991 |

OTHER PUBLICATIONS

Papazyan et al, Selenium in poultry nutrition-effects on fertility and hatchability, Praxis veterinaria 54 (1-2) 85-102, 2006.*
Coman et al, Research regarding the effect of negative aeroions on broilers bred in an intensive system, Stiintifice seria zootehnie medicina veterinara (1986) 30: 107-108.*
Renema, Reproductive response to Sel-Plex organic selenium organic selenium in male and female broiler breeders; impact on production traits and hatchability, Nutritional biotechnology in the feed and food industries. Proceedings of Alltech's 20th annual symposium: re-imagining the feed industry, Lexington, Kentucky, USA, (2004) pp. 81-91.*
Bagnell et al, Relaxin gene expression in the sow corpus luteum during the cycle, pregnancy, and lactation, Endocrinology 126 (5): 2514-2520, 1990.*
Mahan et al, The role of selenium and Sel-Plex in sow production, Nutritional biotechnology in the feed and food industries. Proceedings of Alltech's 20th Annual Symposium: re-imaging the feed industry, Lexington, Kentucky, USA, May 23-26, 2004, pp. 131-139.*
Alliston et al., Follicle stimulating hormone-regulated expression of serum/glucocorticoid-inducible kinase in rat ovarian granulosa cells: a functional role for the Sp1 family in promoter activity, Mol Endocrinol. Dec. 1997;11(13):1934-49.
Bedwal, R. S. et al., "Selenium—its biological perspectives", Medical Hypotheses vol. 41, No. 2, Aug. 1993, pp. 150-159.
Benson and Doubilet, Sonographic prediction of gestational age: accuracy of second- and third-trimester fetal measurements, AJR Am J Roentgenol. Dec. 1991 ;157(6):1275-7.
Betsholtz, Insight into the physiological functions of PDGF through genetic studies in mice, Cytokine Growth Factor Rev. Aug. 2004;15(4):215-28.
Blum et al., Growth hormone is effective in treatment of short stature associated with short stature homeobox-containing gene deficiency: Two-year results of a randomized, controlled, multicenter trial, J Clin Endocrinol Metab. Jan. 2007;92(1):219-28. Epub Oct. 17, 2006.
Bondos, Variations on a theme: Hox and Wnt combinatorial regulation during animal development, Sci STKE. Oct. 3, 2006;2006(355):pe38.
Bracket et al., Relaxin: an ovarian hormone in an avian species (*Gallus domesticus*), Gen Comp Endocrinol. Feb. 1997;105(2):155-63.
Brooks, et al., Plasma selenium level before diagnosis and the risk of prostate cancer development, J Urol. Dec. 2001;166(6):2034-8.
Chang et al., Prediction of the small for gestational age infant: which ultrasonic measurement is best?, Obstet Gynecol. Dec. 1992;80(6):1030-8.
Chudgar et al., Regulation of connective tissue growth factor expression in the aqueous humor outflow pathway, Mol Vis. Sep. 30, 2006;12:1117-26.
Clark et al., Effects of selenium supplementation for cancer prevention in patients with carcinoma of the skin. A randomized controlled trial. Nutritional Prevention of Cancer Study Group, JAMA. Dec. 25, 1996;276(24):1957-63.
Coyle, "Oxidative stress, glutamate, and neurodegenerative disorders" Science vol. 262, 1993, pp. 689-695.
Deleve; Kaplowitz, "Glutathione metabolism and its role in hepatotoxicity" Pharm. Ther. vol. 52, 1991, pp. 287-305.

(Continued)

*Primary Examiner* — Qiuwen Mi
(74) *Attorney, Agent, or Firm* — Valerie L. Calloway; Merchant & Gould PC

(57) ABSTRACT

Compositions comprising selenium (e.g., organic selenium (e.g., selenized yeast (e.g., SEL-PLEX))) and methods of using the same (e.g., as a therapeutic and/or prophylactic treatment) are provided. For example, compositions comprising selenium (e.g., organic selenium (e.g., selenized yeast (e.g., SEL-PLEX))) and methods of using the same are provided for treating and/or preventing one or more conditions (e.g., problems) disorders, and/or diseases related to establishing and/or maintaining a pregnancy. Compositions and methods of the invention find use in, among other things, research and clinical (e.g., preventative and therapeutic) applications.

7 Claims, 5 Drawing Sheets

(56) References Cited

OTHER PUBLICATIONS

DeLise, Cellular interactions and signaling in cartilage development, Osteoarthritis Cartilage. Sep. 2000;8(5):309-34.

Dougherty and Sanders, Estrogen action: revitalization of the chick oviduct model, Trends Endocrinol Metab. Nov. 2005;16(9):414-9. Epub Oct. 3, 2005.

Dschietzig and Stangl, Relaxin: a pregnancy hormone as central player of body fluid and circulation homeostasis, Cell Mol Life Sci. Apr. 2003;60(4):688-700.

Edens et al., Practical applications for selenomethionine: broiler breeder reproduction. In: Nutritional Biotechnology in the Feed and Food Industries: Proceedings of Alltech's 18th Annual Symposium (T.P. Lyons and K.A. Jacques, eds), Nottingham University Press, Nottingham, UK, pp. 29-42, 2002.

El-Bayoumy, K. (1991) The role of selenium in cancer prevention. In: Cancer Principles and Practice of Oncology (DeVita, V. T., Hellman, S. & Rosenberg, S. S., eds.), 4th ed., pp. 1-15. J. B. Lippincott, Philadelphia, PA.

Ferris G. M. Lloyd et al. "The effect of supplementation with selenium and vitamin E in psoriasis" App. Clin. Biochem. vol. 26, 1989, pp. 83-88 G. M. Lloyd, et al., App. Clin. Biochem.,26:83-88 (1989).

Florio et al., Paracrine regulation of endometrial function: interaction between progesterone and corticotropin-releasing factor (CRF) and activin A, Steroids. Nov. 2003;68(10-13):801-7.

Furnsinn et al., "Improved glucose tolerance by acute vanadate but not by selenate exposure in genetically obese rats (fa/fa)" Int. J of Obesity and Related Metab. Dis. vol. 19, No. 7, 1995, pp. 458-463.

Garland et al., "Antioxidant micronutrients and breast cancer" J. Am. Coll Nutr. vol. 12, 1993, pp. 400-11.

Gerloff et al., "Effect of selenium supplementation on dairy cattle" J. Anim. Sci. vol. 70, 1992, pp. 3934-3940.

Ghadirian et al., "A case-control study of toenail selenium and cancer of the breast, colon, and Prostate" Cancer Detect Prev vol. 24, 2000, pp. 305-313.

Goehring et al, "Effects of seleniferous grains and inorganic selenium on tissue and blood composition and growth performance of rats and swine" J. Anim. Sci. vol. 59, 1984, pp. 725-732.

Goldsmith et al., Relaxin regulation of endometrial structure and function in the rhesus monkey, Proc Natl Acad Sci U S A. Mar. 30, 2004;101(13):4685-9. Epub Mar. 19, 2004.

Hombria, Beyond homeosis—HOX function in morphogenesis and organogenesis, Differentiation. Oct. 2003;71 (8):461-76.

Ip and Daniel, Effects of selenium on 7,12-dimethylbenz(a)anthracene-induced mammary carcinogenesis and DNA adduct formation, Cancer Res. Jan. 1985;45(1):61-5.

Ip, Lessons from basic research in selenium and cancer prevention, J Nutr. Nov. 1998;128(11):1845-54.

Jetten et al., The ROR nuclear orphan receptor subfamily: critical regulators of multiple biological processes, Prog Nucleic Acid Res Mol Biol. 2001;69:205-47.

Kleinberg et al., Insulin-like growth factor (IGF)-I controls prostate fibromuscular development: IGF-I inhibition prevents both fibromuscular and glandular development in eugonadal mice, Endocrinology. Mar. 2007;148(3):1080-8. Epub Nov. 30, 2006.

Koos et al., New insight into the transcriptional regulation of vascular endothelial growth factor expression in the endometrium by estrogen and relaxin, Ann N Y Acad Sci. May 2005;1041:233-47.

Krauss et al., Close encounters: regulation of vertebrate skeletal myogenesis by cell-cell contact, J Cell Sci. Jun. 1, 2005;118(Pt 11):2355-62.

Lepercq and Mahieu-Caputo, Diagnosis and management of intrauterine growth retardation, Horm Res. 1998;49 Suppl 2:14-9.

Li et al., Gene regulation by Sp1 and Sp3, Biochem Cell Biol. Aug. 2004;82(4):460-71.

Machelon et al., [Granulosa cells as indicators of oocyte quality], J Gynecol Obstet Biol Reprod (Paris). Sep. 2006;35(5 Pt 2):2S14-2S18.

Mahan and Peters, Long-term effects of dietary organic and inorganic selenium sources and levels on reproducing sows and their progeny, J Anim Sci 2004. 82:1343-1358.

Mahan, D.C. 1999. Organic selenium: using nature's model to redefine selenium supplementation for animals. In: Biotechnology in the Feed Industry. Proc. 15th Annual Symposium (T.P. Lyons and K.A. Jacques, eds.). Nottingham University Press, Nottingham, UK, pp. 523-535.

Mark et al., Function of retinoid nuclear receptors: lessons from genetic and pharmacological dissections of the retinoic acid signaling pathway during mouse embryogenesis, Annu Rev Pharmacol Toxicol. 2006;46:451-80.

Mehler, Mechanisms regulating lineage diversity during mammalian cerebral cortical neurogenesis and gliogenesis, Results Probl Cell Differ. 2002;39:27-52.

Meister; Anderson, Glutathione, Annual Review of Biochemistry, vol. 52: 711-760 (Volume publication date Jul. 1983).

Nemer and Horb, The KLF family of transcriptional regulators in cardiomyocyte proliferation and differentiation, Cell Cycle. Jan. 15, 2007;6(2):117-21. Epub Jan. 13, 2007.

Palmer; Paulson, "Reactive oxygen species and antioxidants in signal transduction and gene Expression" Nutr. Rev. vol. 55, 1997, pp. 353-361.

Pence et al., Effects of dietary selenium on UVB-induced skin carcinogenesis and epidermal antioxidant status, J Invest Dermatol. May 1994;102(5):759-61.

Poole et al., The role of FGF and VEGF in angioblast induction and migration during vascular development, Dev Dyn. Jan. 2001;220(1):1-17.

Salonen et al., Association between serum selenium and the risk of cancer, Am J Epidemiol. Sep. 1984;120(3):342-9.

Shirota et al., Relaxin-induced angiogenesis in ovary contributes to follicle development, Ann N Y Acad Sci. May 2005;1041:144-6.

Stephenson et al., snf1lk encodes a protein kinase that may function in cell cycle regulation, Genomics. Jun. 2004;83 (6)1105-15.

Underhill et al., Retinoid signalling and skeletal development, Novartis Found Symp. 2001;232:171-85; discussion 185-8.

Virtamo et al., "Serum selenium and risk of cancer. A prospective follow-up of nine years" Cancer vol. 60, 1987, pp. 145-148.

Wang et al., Insulin-like growth factor-II (IGF-II), IGF-binding protein-3 (IGFBP-3), and IGFBP-4 in follicular fluid are associated with oocyte maturation and embryo development, Fertil Steril. Nov. 2006;86(5):1392-401.

Willett et al., Prediagnostic serum selenium and risk of cancer, Lancet. Jul. 16, 1983;2(8342):130-4.

Yoshizawa et al., Study of prediagnostic selenium level in toenails and the risk of advanced prostate cancer, J Natl Cancer Inst. Aug. 19, 1998;90(16):1219-24.

Yu et al., Protective role of selenium against hepatitis B virus and primary liver cancer in Qidong, Biol Trace Elem Res. Jan. 1997;56(1):117-24.

Zarrow, Relaxin Content of Blood, Urine and Other Tissues of Pregnant and Postpartum Guinea Pigs, Exp Biol Med (Maywood), Proceedings of the Society for Experimental Biology and Medicine, Nov. 1947 66: 488-491.

* cited by examiner

| Gene | SS | SP |
|---|---|---|
| Glutathione Peroxidase 3 | 1.4 (NS)* | 2.07(p<0.01) |
| Glutathione Peroxidase 4 | 1.79(p<0.05) | 2.12(p<0.01) |

*NS = Non-Significant

FIGURE 2

Fold Change

| Gene Title | Biological Process | SodSel | Sel-Plex |
|---|---|---|---|
| Fibroblast growth factor 1 (acidic) (FGF1) | Angiogenesis, cell proliferation/differentiation, embryonic development, organogenesis, tissue repair | +1.02 | +6.87 |
| Fibroblast growth factor 2 (basic) (FGF2) | Limb and nervous system development, cell cycle regulation, wound healing | +1.75 | +2.50 |
| SNF1-like kinase | Regulation of insulin receptor signaling, cell cycle regulation, muscle growth/differentiation | +1.81 | +3.41 |
| Platelet-derived growth factor alpha (PDGFA) | Growth factor activity, regulation of progression through the cell cycle, cell proliferation | +1.54 | +1.94 |
| Cyclin D1 (CCND1) | Cell cycle, cell division regulation | +1.51 | +2.01 |
| Activin A receptor, type 1 (ACVR1) | Activin signaling, FSH production, follicular development in ovary | +1.19 | +1.60 |

FIGURE 3

| Gene Title | Biological Process | Fold Change | |
|---|---|---|---|
| | | SodSel | Sel-Plex |
| Sp3 transcription factor (SP3) | Regulation of transcription | +1.07 | +1.58 |
| Homeobox A7 (HOXA7) | Developmental transcription factor | +1.46 | +1.75 |
| Homeobox D12 (HOXD12) | Multicellular organismal development transcription factor activity | +1.92 | +1.82 |
| Transforming growth factor beta receptor I (TGFBR1) | Serine/threonine kinase signaling, transforming growth factor beta receptor activity | +1.08 | +1.36 |
| Retinoic acid receptor beta (RARB) | Vertebrate development, steroid hormone receptor/retinoic acid receptor activity, transcription neural tube development in embryo | +1.17 | +1.71 |
| Insulin-like growth factor binding protein 7 (IGFBP7) | Regulation on cell growth, insulin-like growth factor binding | +1.06 | +1.4 |

| Gene | FC SS | FC SP |
|---|---|---|
| Protein Kinase A | + 2.23 (p<0.05) | +1.70 (p<0.05) |
| SP3 | +1.07 (NS) | +1.58 (p<0.05) |
| Sgk | -0.83 (NS) | +3.58 (p<0.05) |

COMPOSITIONS AND METHODS FOR ESTABLISHING AND/OR MAINTAINING PREGNANCY

This application claims the benefit of and priority to U.S. Provisional Patent Application Ser. No. 60/930,752 filed May 18, 2007, hereby incorporated by reference in its entirety.

FIELD OF THE INVENTION

The present invention relates to compositions comprising selenium (e.g., organic selenium (e.g., selenized yeast (e.g., SEL-PLEX))) and methods of using the same (e.g., as a therapeutic and/or prophylactic treatment). For example, the present invention provides compositions comprising selenium (e.g., organic selenium (e.g., selenized yeast (e.g., SEL-PLEX))) and methods of using the same for treating and/or preventing one or more conditions (e.g., problems) disorders, and/or diseases related to establishing and/or maintaining a pregnancy. Compositions and methods of the present invention find use in, among other things, research, agriculture, and clinical (e.g., preventative and therapeutic) applications.

BACKGROUND OF THE INVENTION

Infertility and other complications related to pregnancy are a major problem in the United States and abroad in human and non-human populations. It is estimated that around 10 million individuals are affected by infertility and/or other conditions related to the inability to conceive and/or have children.

A wide variety of factors are thought to reduce and/or obstruct fertility including, among other things, genetic factors, physical factors, health, age, diet, stress, and drug and alcohol consumption.

For example, when a woman ages, her reproductive system (e.g., comprising the reproductive tract, uterus, and ova) also ages. As a woman ages, she may become less likely to become pregnant and if she does become pregnant, she runs the risk of having complications related to the pregnancy.

What is needed are compositions and methods for increasing fertility (e.g., increasing conditions favorable for establishing and/or maintaining pregnancy (e.g., in human and non-human species (e.g., mammals, birds, etc.))).

SUMMARY OF THE INVENTION

The present invention relates to compositions comprising selenium (e.g., organic selenium (e.g., selenized yeast (e.g., SEL-PLEX))) and methods of using the same (e.g., as a therapeutic and/or prophylactic treatment). For example, the present invention provides compositions comprising selenium (e.g., organic selenium (e.g., selenized yeast (e.g., SEL-PLEX))) and methods of using the same for treating and/or preventing one or more conditions (e.g., problems) disorders, and/or diseases related to establishing and/or maintaining a pregnancy. Compositions and methods of the present invention find use in, among other things, research, agriculture, and clinical (e.g., preventative and therapeutic) applications.

Accordingly, in some embodiments, the present invention provides a method of treating and/or preventing a condition (e.g., a problem) a disorder, and/or a disease related to establishing and/or maintaining a pregnancy comprising administrating to a subject a composition comprising selenium (e.g., organic selenium (e.g., selenized yeast (e.g., SEL-PLEX))), for example, under conditions such that the expression of one or more genes involved in establishing and/or maintaining pregnancy are altered (e.g., enhanced) in the subject.

In some embodiments, the present invention provides a method of altering expression of one or more genes associated with establishment of and/or maintenance of pregnancy in a subject comprising: providing a subject; and a composition comprising selenium, wherein the selenium is present within a dried, nonviable selenium-enriched yeast; and administering the composition to the subject under conditions such that the expression of one or more genes associated with establishment of and/or maintenance of pregnancy is enhanced in the subject compared to a control subject. In some embodiments, the control subject is not administered selenium. In some embodiments, the control subject is administered a composition comprising selenium, wherein the selenium is not present in a dried, nonviable selenium-enriched yeast. In some embodiments, the one or more genes associated with establishment of and/or maintenance of pregnancy is relaxin. In some embodiments, the one or more genes associated with establishment of and/or maintenance of pregnancy is serum and glucocorticoid inducible-protein kinase (sgk). In some embodiments, enhancing expression of one or more genes associated with establishment of and/or maintenance of pregnancy reduces and/or eliminates the risk of perinatal morbidity and/or mortality in the subject. In some embodiments, enhancing expression of one or more genes associated with establishment of and/or maintenance of pregnancy increases fetal growth in the subject. In some embodiments, increasing fetal growth in the subject comprises increasing fetal growth rate in the subject. In some embodiments, enhancing expression of one or more genes associated with establishment of and/or maintenance of pregnancy increases the duration of gestation in the subject. In some embodiments, enhancing expression of one or more genes associated with establishment of and/or maintenance of pregnancy promotes the health of the uterus. In some embodiments, promoting the health of the uterus comprises promoting connective tissue formation and/or rearrangement. In some embodiments, enhancing expression of one or more genes associated with establishment of and/or maintenance of pregnancy promotes proper formation of the pubis. In some embodiments, enhancing expression of one or more genes associated with establishment of and/or maintenance of pregnancy promotes the health of the embryo and/or fetus in the subject. In some embodiments, promoting the health of the embryo and/or fetus in the subject comprises promoting limb and nervous system development. In some embodiments, promoting the health of the embryo and/or fetus in the subject comprises promoting muscle growth and differentiation. In some embodiments, promoting the health of the embryo and/or fetus in the subject comprises promoting neural tube development. In some embodiments, enhancing expression of one or more genes associated with establishment of and/or maintenance of pregnancy reduces the risk of and/or incidence of an event selected from the group comprising spontaneous abortion, miscarriage, and birthing complications. In some embodiments, the subject is a human. In some embodiments, the subject is a non-human mammal. In some embodiments, the subject is a subject from an avian species. In some embodiments, the subject is a subject from an aquatic species. In some embodiments, the expression is enhanced two fold or greater in the subject compared to the control subject. In some embodiments, expression is enhanced three fold or greater in the subject compared to the control subject. In some embodiments, the expression is enhanced greater than two fold (e.g., three fold, four fold, five fold, six fold or more) in the subject compared to the control subject. In some embodiments, expression is enhanced three fold or greater in the subject compared to the control subject. In some embodiments, the composition comprising selenium is administered in such a way so as to provide between 100 and 400 µg of selenium to the subject each day, although embodiments in which greater than 400 µg and less than 100 µg are administered are also contemplated. In some embodiments, the composition comprising selenium is administered in such a way so as to provide 200 µg of selenium to the subject each day. In some embodiments, the subject is administered the composition for a period of no less than 6 months prior to establishing and/or attempting to establishing a pregnancy. In some embodiments, a subject is administered the composition for more than 9 months, more than 12 months, more than 18 months, or more than two years prior to establishing and/or attempting to establish a pregnancy. In some embodiments, a subject is administered a composition of the present invention for less than six months prior to establishing and/or attempting to establish a pregnancy. In some embodiments, the subject is administered the composition during pregnancy. In some embodiments, the one or more genes associated with establishment of and/or maintenance of pregnancy in a subject are selected from the group comprising fibroblast growth factor 2 (FGF2), SNF1-like kinase, platelet-derived growth factor alpha (PDFGA), cyclin D1 (CCND1), activin A receptor type 1 (ACVR1), Sp3 transcription factor (SP3), homeobox A7, homeobox D12, retinoic acid receptor beta (RARB), insulin-like growth factor binding protein 7, and Protein Kinase A.

The present invention also provides a method of treating a subject comprising: identifying a subject that will benefit from the treatment; providing: the subject; and a composition comprising selenium, wherein the selenium is present within a dried, nonviable selenium-enriched yeast; and administering the composition to the subject under conditions such that the expression of one or more genes associated with establishment of and/or maintenance of pregnancy is enhanced in the subject compared to a control subject. In some embodiments, identifying the subject comprises detecting the level of expression of one or more genes associated with establishment of and/or maintenance of pregnancy. In some embodiments, the one or more genes associated with establishment of and/or maintenance of pregnancy is relaxin. In some embodiments, the one or more genes associated with establishment of and/or maintenance of pregnancy is serum and glucocorticoid inducible-protein kinase (sgk). In some embodiments, the one or more genes associated with establishment of and/or maintenance of pregnancy is selected from the group comprising fibroblast growth factor 2 (FGF2), SNF1-like kinase, platelet-derived growth factor alpha (PD-FGA), cyclin D1 (CCND1), activin A receptor type 1 (ACVR1), Sp3 transcription factor (SP3), homeobox A7, homeobox D12, retinoic acid receptor beta (RARB), insulin-like growth factor binding protein 7, and Protein Kinase A. In some embodiments, detecting the level of expression of one or more genes associated with establishment of and/or maintenance of pregnancy comprises detecting nucleic acid expression and/or protein expression. In some embodiments, the method further comprises: d) detecting the level of one or more genes associated with establishment of and/or maintenance of pregnancy after administration of the composition. The present invention contemplates the identification of different types of subjects that may benefit from the compositions and methods disclosed herein including, but not limited to, a subject desiring reduction and/or elimination of the risk of perinatal morbidity and/or mortality; a subject desiring an increase in fetal growth in the subject; a subject desiring an increase in fetal growth rate in the subject; a subject desiring an increase in the duration of gestation in the subject; a subject desiring the promotion of connective tissue formation and/or rearrangement in the subject; a subject desiring promotion of proper formation of the pubis; a subject desiring the promotion of the health of the embryo and/or fetus in the subject; a subject desiring promotion of limb and nervous system development in an embryo and/or fetus in the subject; a subject desiring promotion of muscle growth or differentiation in an embryo and/or fetus in the subject; a subject desiring promotion of neural tube development in an embryo and/or fetus in the subject; a subject desiring a reduction in the risk and/or incidence of spontaneous abortion; a subject desiring a reduction in the risk and/or incidence of miscarriage; a subject desiring a reduction in the risk and/or incidence of stillbirth; and a subject desiring a reduction in the risk and/or incidence of birthing complications.

In some embodiments, the composition comprising selenium (e.g., organic selenium (e.g., selenized yeast (e.g., SEL-PLEX))) comprises one or more other forms of selenium. The present invention is not limited by the type of selenium co-administered. Indeed, a variety of forms of selenium are contemplated to be useful in co-administration including, but not limited to, selenomethionine, selenocysteine, a selenite compound, a selenate compound, or derivatives, salts, or modifications thereof. In some embodiments, providing selenium (e.g., organic selenium (e.g., selenized yeast (e.g., SEL-PLEX))) and one or more different forms of selenium provides an additive benefit (e.g., enhancement of gene expression) to the subject. In some embodiments, providing selenium (e.g., organic selenium (e.g., selenized yeast (e.g., SEL-PLEX))) and one or more different forms of selenium provides a synergistic (e.g., more than additive) benefit (e.g., enhancement of gene expression) to the subject. In some embodiments, providing selenium (e.g., organic selenium (e.g., selenized yeast (e.g., SEL-PLEX))) and one or more different forms of selenium provides altered (e.g., enhanced) expression of more genes than are altered (e.g., enhanced) with either form of selenium alone.

The present invention is not limited by the amount of selenium (e.g., organic selenium (e.g., selenized yeast (e.g., SEL-PLEX))) administered to a subject. Indeed a variety of different doses are contemplated to be useful in the present invention. In some embodiments, the composition comprising selenium (e.g., organic selenium (e.g., selenized yeast (e.g., SEL-PLEX))) is administered to the subject so as to provide between 25-800 µg of selenium to the subject each day. In some embodiments, the composition comprising selenium (e.g., organic selenium (e.g., selenized yeast (e.g., SEL-PLEX))) is administered to the subject so as to provide between 200-400 µg of selenium to the subject each day. In other embodiments, the composition comprising selenium (e.g., organic selenium (e.g., selenized yeast (e.g., SEL-PLEX))) is administered to the subject so as to provide between 25 and 75 µg of selenium to the subject each day. In some embodiments, a composition comprising two or more different forms of selenium (e.g., selonmethionine, Sod-sel and/or SEL-PLEX) is administered to a subject so as to provide the subject between 25 and 5000 µg of selenium each day.

DESCRIPTION OF THE DRAWINGS

FIG. 2 shows the changes in expression profiles of multiple genes involved in reproduction and embryogenesis in response to sodium selenite or SEL-Plex. The numbers indicate Fold Change (FC) relative to selenium deficiency, grey background indicates a statistically significant up-regulation (p<0.05) and the black background no significant change relative to selenium deficiency.

FIG. 3 shows the changes in expression profiles of multiple genes involved in reproduction and embryogenesis in response to sodium selenite or SEL-PLEX administration. The numbers indicate Fold Change (FC) relative to selenium deficiency, grey background indicates a statistically significant up-regulation (p<0.05) and the black background no significant change relative to selenium deficiency.

DEFINITIONS

Figure 1:
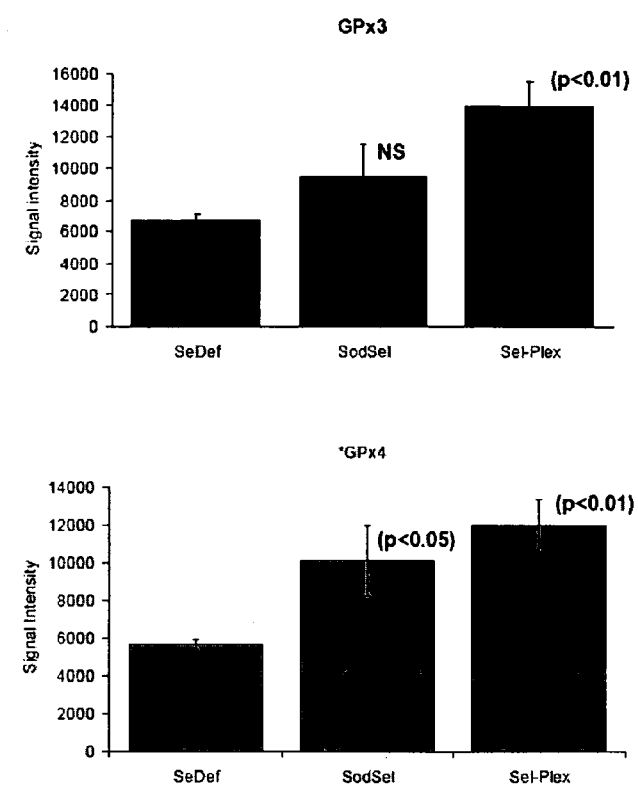
FIG. 1 shows the fold change (FC) in the expression of GSH-PX genes in oviduct, relative to selenium deficient hens induced by sodium selenite (SS) and SEL-PLEX (SP).

As used herein, the terms "pregnant subject," "pregnancy" and "pregnant" (e.g., when used in reference to a subject) refers to a subject (e.g., human or non-human mammal, avian species, aquatic species (e.g., fish)) carrying one or more developing offspring within its body. The pregnant subject may have conceived naturally or may have become pregnant through an artificial technique (e.g., artificial reproductive technology (e.g., in vitro fertilization or embryo transfer)). The developing offspring may be at any stage of gestation (e.g., embryonic or fetal stage (e.g., depending upon how much time has passed since fertilization (e.g., in humans, this transition occurs at about eight weeks following implantation of the embryo))).

As used herein, the term "mammal" refers to any of the various warm-blooded vertebrate animals of the class Mammalia.

As used herein, the term "gestation" refers to the period of development in the uterus from the time of conception until parturition/birth, and "gestational age" refers to the length of this time period.

Conception refers to the formation of one or more viable zygotes through the union of sperm and egg.

Birth refers to the emergence and separation of offspring from the mother, whether by natural or assisted means.

As used herein, the terms "peptide," "polypeptide" and "protein" refer to a primary sequence of amino acids that are joined by covalent "peptide linkages." In general, a peptide consists of a few amino acids, typically from 2-50 amino acids, and is shorter than a protein. The term "polypeptide" encompasses peptides and proteins. In some embodiments, the peptide, polypeptide or protein is synthetic, while in other embodiments, the peptide, polypeptide or protein are recombinant or naturally occurring. A synthetic peptide is a peptide that is produced by artificial means in vitro (i.e., was not produced in vivo).

The terms "sample" and "specimen" are used in their broadest sense and encompass samples or specimens obtained from any source. As used herein, the term "sample" is used to refer to biological samples obtained from animals (including humans), and encompasses fluids, solids, tissues, and gases. In some embodiments of this invention, biological samples include cerebrospinal fluid (CSF), serous fluid, urine, saliva, blood, and blood products such as plasma, serum and the like. However, these examples are not to be construed as limiting the types of samples that find use with the present invention.

As used herein, the terms "selenium-enriched yeast" and "selenized yeast" refer to any yeast (e.g., *Saccharomyces cerevisiae*) that is cultivated in a medium containing inorganic selenium salts. The present invention is not limited by the selenium salt used. Indeed, a variety of selenium salts are contemplated to be useful in the present invention including, but not limited to, sodium selenite, sodium selenate, cobalt selenite or cobalt selenate. Free selenomethionine (e.g., not associated with a cell or yeast) can also be used as the selenium source for selenium enriched yeast as yeast does incorporate this form of selenium. During cultivation, because of the chemical similarity between selenium and sulfur, yeast incorporate selenium in place of sulfur in what are normally sulfur-containing organic compounds within the cell. A selenium-containing compound in such yeast preparations is selenomethionine which will be present in a form that is incorporated into polypeptides/proteins. The amount of total cellular selenium present in the form of selenomethionine in such preparations will vary, but can be between 10 and 100%, 20-60%, 50-75% and between 60 and 75%. The remainder of the organic selenium in selenized yeast preparations is predominantly made up of intermediates in the pathway for selenomethionine biosynthesis. These include, but are not limited to, selenocysteine, selenocystathionine, selenohomocysteine and seleno-adenosylselenomethionine. The amount of residual inorganic selenium salt in the finished product is generally quite low (e.g., <2%). However, the present invention is not limited by this percentage, as preparations that contain more (e.g., between 2 and 70%) or less (e.g., between 0.1 and 2%) than this percentage are also encompassed by the invention.

As used herein, the term "SEL-PLEX" refers to a dried, nonviable selenium-enriched yeast (e.g., Sacchoromyces cerevisiae of accession number CNCM I-3060, Collection Nationale De Cultures De Microorganismes (CNCM), Institut Pasteur, Paris, France) cultivated in a fed-batch fermentation that provides incremental amounts of cane molasses and selenium salts in a manner that minimizes the detrimental effects of selenium salts on the growth rate of the yeast and allows for optimal incorporation of inorganic selenium into cellular organic material. Residual inorganic selenium is eliminated (e.g., using a rigorous washing process) and does not exceed 2% of the total selenium content.

As used herein, the term "organic selenium" refers to any organic compound wherein selenium replaces sulfur. Thus, organic selenium can refer to any such compound biosynthesized by yeast, or it can refer to free organic seleno-compounds that are chemically synthesized. An example of the latter is free selenomethionine.

As used herein, the term "inorganic selenium" generally refers to any selenium salt (e.g., sodium selenite, sodium selenate, cobalt selenite and cobalt selenate). There are also a variety of other inorganic selenium sources (See e.g., those listed in the Merck index). Selenized yeast may be generated using a source of inorganic selenium including, but not limited to, sodium selenite, sodium selenate, cobalt selenite, cobalt selenate, selenic acid, selenious acid, selenium bromide, selenium chloride, selenium hexafluoride, selenium oxide, selenium oxybromide, selenium oxychloride, selenium oxyfluoride, selenium sulfides, selenium tetrabromide, selenium tetrachloride and selenium tetrafluoride.

As used herein, the term "oxidative stress" refers to the cytotoxic effects of oxygen radicals (e.g., superoxide anion ($O_2^-$), hydroxy radical (OH), and hydrogen peroxide ($H_2O_2$)), generated, for example, as byproducts of metabolic processes that utilize molecular oxygen (See e.g., Coyle et al., Science 262:689-695 (1993)).

As used herein, the terms "host," "subject" and "patient" refer to any animal, including but not limited to, human and non-human animals (e.g., dogs, cats, cows, horses, sheep, goats, swine, avian species (e.g., domesticated fowl (e.g., chickens, turkeys, ducks, geese, and guinea fowl, etc.) and other game birds (e.g., quail, pheasants, grouse, partridges, emu, ostriches, pigeons, etc.), as well as aquatic species (e.g., fresh water and marine (salt water) species (e.g., including, but not limited to, fish (e.g., bass, catfish, carp, cod, crappie, eel, flounder, grouper, haddock, halibut, herring, kingfish, mackerel, mahi mahi, orange roughy, perch, pike, Pollock, salmon, sardine, shark, snapper, sole, tilapia, trout, tuna, and walleye), crustaceans (e.g., crab, crayfish, lobster, prawn, and shrimp), mollusks, etc.) that is studied, analyzed, tested, diagnosed or treated (e.g., using the compositions and methods of the present invention). As used herein, the terms "host," "subject" and "patient" are used interchangeably, unless indicated otherwise.

As used herein, the term "antibody" (or "antibodies") refers to any immunoglobulin that binds specifically to an antigenic determinant, and specifically binds to proteins identical or structurally related to the antigenic determinant that stimulated their production. Thus, antibodies can be useful in assays to detect the antigen that stimulated their production. Monoclonal antibodies are derived from a single clone of B lymphocytes (i.e., B cells), and are generally homogeneous in structure and antigen specificity. Polyclonal antibodies originate from many different clones of antibody-producing cells, and thus are heterogenous in their structure and epitope specificity, but all recognize the same antigen. In some embodiments, monoclonal and polyclonal antibodies are used as crude preparations, while in preferred embodiments, these antibodies are purified. For example, in some embodiments, polyclonal antibodies contained in crude antiserum are used. Also, it is intended that the term "antibody" encompass any immunoglobulin (e.g., IgG, IgM, IgA, IgE, IgD, etc.) obtained from any source (e.g., humans, rodents, non-human primates, lagomorphs, caprines, bovines, equines, ovines, etc.).

As used herein, the terms "auto-antibody" or "auto-antibodies" refer to any immunoglobulin that binds specifically to an antigen that is native to the host organism that produced the antibody (i.e., the antigen is directed against "self" antigens). The presence of auto-antibodies is referred to herein as "autoimmunity."

As used herein, the term "antigen" is used in reference to any substance that is capable of being recognized by an antibody. It is intended that this term encompass any antigen and "immunogen" (i.e., a substance that induces the formation of antibodies). Thus, in an immunogenic reaction, antibodies are produced in response to the presence of an antigen or portion of an antigen. The terms "antigen" and "immunogen" are used to refer to an individual macromolecule or to a homogeneous or heterogeneous population of antigenic macromolecules. It is intended that the terms antigen and immunogen encompass protein molecules or portions of protein molecules, that contains one or more epitopes. In many cases, antigens are also immunogens, thus the term "antigen" is often used interchangeably with the term "immunogen." In some preferred embodiments, immunogenic substances are used as antigens in assays to detect the presence of appropriate antibodies in the serum of an immunized animal.

As used herein, the terms "antigen fragment" and "portion of an antigen" and the like are used in reference to a portion of an antigen. Antigen fragments or portions typically range in size, from a small percentage of the entire antigen to a large percentage, but not 100%, of the antigen. However, in situations where "at least a portion" of an antigen is specified, it is contemplated that the entire antigen is also present (e.g., it is not intended that the sample tested contain only a portion of an antigen). In some embodiments, antigens, antigen fragments and/or portions thereof, comprise an "epitope" recognized by an antibody, while in other embodiments these fragments and/or portions do not comprise an epitope recognized by an antibody. In addition, in some embodiments, antigen fragments and/or portions are not immunogenic, while in preferred embodiments, the antigen fragments and/or portions are immunogenic.

The terms "antigenic determinant" and "epitope" as used herein refer to that portion of an antigen that makes contact with a particular antibody variable region. When a protein or fragment (or portion) of a protein is used to immunize a host animal, numerous regions of the protein are likely to induce the production of antibodies that bind specifically to a given region or three-dimensional structure on the protein (these regions and/or structures are referred to as "antigenic determinants"). In some settings, antigenic determinants compete with the intact antigen (i.e., the "immunogen" used to elicit the immune response) for binding to an antibody.

The terms "specific binding" and "specifically binding" when used in reference to the interaction between an antibody and an antigen describe an interaction that is dependent upon the presence of a particular structure (i.e., the antigenic determinant or epitope) on the antigen. In other words, the antibody recognizes and binds to a protein structure unique to the antigen, rather than binding to all proteins in general (i.e., non-specific binding).

As used herein, the term "immunoassay" refers to any assay that uses at least one specific antibody for the detection or quantitation of an antigen. Immunoassays include, but are not limited to, Western blots, ELISAs, radio-immunoassays, and immunofluorescence assays.

The terms "Western blot," "Western immunoblot" "immunoblot" and "Western" refer to the immunological analysis of protein(s), polypeptides or peptides that have been immobilized onto a membrane support. The proteins are first resolved by polyacrylamide gel electrophoresis (i.e., SDS-PAGE) to separate the proteins, followed by transfer of the protein from the gel to a solid support, such as nitrocellulose or a nylon membrane. The immobilized proteins are then exposed to an antibody having reactivity towards an antigen of interest. The binding of the antibody (i.e., the primary antibody) is detected by use of a secondary antibody that specifically binds the primary antibody. The secondary antibody is typically conjugated to an enzyme that permits visualization of the antigen-antibody complex by the production of a colored reaction product or catalyzes a luminescent enzymatic reaction (e.g., the ECL reagent, Amersham).

As used herein, the term "ELISA" refers to enzyme-linked immunosorbent assay (or EIA). Numerous ELISA methods and applications are known in the art, and are described in many references (See, e.g., Crowther, "Enzyme-Linked Immunosorbent Assay (ELISA)," in Molecular Biomethods Handbook, Rapley et al. (eds.), pp. 595-617, Humana Press, Inc., Totowa, N.J. (1998); Harlow and Lane (eds.), Antibodies: A Laboratory Manual, Cold Spring Harbor Laboratory Press (1988); Ausubel et al. (eds.), Current Protocols in Molecular Biology, Ch. 11, John Wiley & Sons, Inc., New York (1994)). In addition, there are numerous commercially available ELISA test systems.

As used herein, the terms "reporter reagent," "reporter molecule," "detection substrate" and "detection reagent" are used in reference to reagents that permit the detection and/or quantitation of an antibody bound to an antigen. For example, in some embodiments, the reporter reagent is a calorimetric substrate for an enzyme that has been conjugated to an antibody. Addition of a suitable substrate to the antibody-enzyme conjugate results in the production of a calorimetric or fluorimetric signal (e.g., following the binding of the conjugated antibody to the antigen of interest). Other reporter reagents include, but are not limited to, radioactive compounds. This definition also encompasses the use of biotin and avidin-based compounds (e.g., including but not limited to neutravidin and streptavidin) as part of the detection system.

As used herein, the term "signal" is used generally in reference to any detectable process that indicates that a reaction has occurred, for example, binding of antibody to antigen. It is contemplated that signals in the form of radioactivity, fluorimetric or calorimetric products/reagents will all find use with the present invention. In various embodiments of the present invention, the signal is assessed qualitatively, while in alternative embodiments, the signal is assessed quantitatively.

As used herein, the term "solid support" is used in reference to any solid or stationary material to which reagents such as antibodies, antigens, and other test components are attached. For example, in an ELISA method, the wells of microtiter plates provide solid supports. Other examples of solid supports include microscope slides, coverslips, beads, particles, cell culture flasks, as well as many other suitable items.

As used herein, the term "characterizing tissue in a subject" refers to the identification of one or more properties of a tissue sample. In some embodiments, tissues are characterized by the identification of the expression, or lack thereof, of various genes described in detail herein.

As used herein, the term "reagent(s) capable of specifically detecting gene expression" refers to reagents capable of or sufficient to detect the expression of various genes described in detail herein (e.g., including, but not limited to, SelW, Sepn1, SelR, Sod2, Dio2, Glo1, Phb, Lhx8, TGF-β1, glutathione peroxidases, fibroblast growth factor 1 (FGF1), fibroblast growth factor 2 (FGF2), SNF1-like kinase, platelet-derived growth factor alpha (PDFGA), cyclin D1 (CCND1), activin A receptor type 1 (ACVR1), Sp3 transcription factor (SP3), homeobox A7, homeobox D12, retinoic acid receptor beta (RARB), insulin-like growth factor binding protein 7, Protein Kinase A, Serum and Glucocorticoid inducible-protein kinase (Sgk), and relaxin). Examples of suitable reagents include, but are not limited to, nucleic acid probes capable of specifically hybridizing to mRNA or cDNA, and antibodies (e.g., monoclonal or polyclonal antibodies).

As used herein, the term "effective amount" refers to the amount of a composition (e.g., comprising selenium (e.g., SEL-PLEX)) sufficient to effect beneficial or desired results. For example, in the case of pregnancy, an "effective amount" is an amount necessary to improve the likelihood of establishing and/or maintaining pregnancy (e.g., from embryonic to fetal state, or from first to second trimester, or from second to third trimester, etc.). In some embodiments, an effective amount is sufficient to achieve a successful result in at least 55%, at least 65%, at least 75%, at least 85%, or at least 95% of the occasions administered (e.g., in the absence of other factors). An effective amount can be administered in one or more administrations, applications or dosages and is not intended to be limited to a particular formulation or administration route.

As used herein, the terms "administration" and "administering" refer to the act of giving a drug, prodrug, or other agent, or therapeutic treatment (e.g., compositions of the present invention) to a subject (e.g., a subject or in vivo, in vitro, or ex vivo cells, tissues, and organs). Exemplary routes of administration to the human body can be through the mouth (oral), through the eyes (ophthalmic), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the terms "co-administration" and "co-administering" refer to the administration of at least two agent(s) (e.g., composition comprising SEL-PLEX and one or more other agents (e.g., embryonic and/or fetal nutrient and/or medicament, or, a second form of selenium) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "treatment" or grammatical equivalents encompasses the improvement and/or reversal of symptoms of disease and/or disorder related to, and/or a problem with establishing and/or maintaining a pregnancy (e.g., intrauterine growth retardation, placental and/or corpus luteum insufficiency,). A compound that causes an improvement in any parameter associated with a disease, disorder, or a problem (e.g., with establishing and/or maintaining a pregnancy) when used in the screening methods of the instant invention may thereby be identified as a therapeutic compound. The term "treatment" refers to both therapeutic treatment and prophylactic or preventative measures. For example, those who may benefit from treatment with compositions and methods of the present invention include those already identified as having a disease, disorder, or a problem (e.g., with establishing and/or maintaining a pregnancy) as well as those in which a disease, disorder, or a problem (e.g., with establishing and/or maintaining a pregnancy) is to be prevented (e.g., using a prophylactic treatment of the present invention).

As used herein, the term "at risk for having a problem with establishing and/or maintaining a pregnancy" refers to a subject (e.g., a human) that is predisposed to experiencing a problem with establishing and/or maintaining a pregnancy. This predisposition may be genetic (e.g., a particular genetic tendency to experience a problem with establishing and/or maintaining a pregnancy, such as heritable disorders), or due to other factors (e.g., age, prior experience of a problem with establishing and/or maintaining a pregnancy, drug or alcohol use, environmental conditions, exposures to detrimental compounds present in the environment, etc.). Thus, it is not intended that the present invention be limited to any particular risk, nor is it intended that the present invention be limited to any particular problem with establishing and/or maintaining a pregnancy.

As used herein, the term "experiencing a problem with establishing and/or maintaining a pregnancy" refers to a subject (e.g., a human) that is experiencing a particular problem with establishing and/or maintaining a pregnancy. It is not intended that the present invention be limited to any particular signs or symptoms, nor problem. Thus, it is intended that the present invention encompass subjects that are experiencing any type of problem related to establishing and/or maintaining a pregnancy wherein the subject exhibits at least some indicia (e.g., sign and/or symptom) associated with the problem with establishing and/or maintaining a pregnancy.

As used herein, the terms "disease" and "pathological condition" are used interchangeably to describe a state, signs, and/or symptoms that are associated with any impairment of the normal state of a living animal or of any of its organs or tissues that interrupts or modifies the performance of normal functions, and may be a response to environmental factors (such as malnutrition, industrial hazards, or climate), to specific infective agents (such as worms, bacteria, or viruses), to inherent defect of the organism (such as various genetic anomalies, or to combinations of these and other factors.

The term "compound" refers to any chemical entity, pharmaceutical, drug, and the like that can be used to treat or prevent a disease, illness, sickness, problem with establishing and/or maintaining a pregnancy, or disorder of bodily function. Compounds comprise both known and potential therapeutic compounds. A compound can be determined to be therapeutic by screening using the screening methods of the present invention. A "known therapeutic compound" refers to a therapeutic compound that has been shown (e.g., through animal trials or prior experience with administration to humans) to be effective in such treatment. In other words, a known therapeutic compound is not limited to a compound efficacious in the treatment of disease (e.g., neurodegenerative disease).

As used herein, the term "kit" is used in reference to a combination of reagents and other materials. It is contemplated that the kit may include reagents such as nutrients and drugs as well as administration means. It is not intended that the term "kit" be limited to a particular combination of reagents and/or other materials.

As used herein, the term "toxic" refers to any detrimental or harmful effects on a subject, a cell, or a tissue as compared to the same cell or tissue prior to the administration of the toxicant.

As used herein, the term "pharmaceutical composition" refers to the combination of an active agent (e.g., composition comprising SEL-PLEX) with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "topically" refers to application of the compositions of the present invention to the surface of the skin and mucosal cells and tissues (e.g., alveolar, buccal, lingual, masticatory, or nasal mucosa, and other tissues and cells that line hollow organs or body cavities).

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintrigrants (e.g., potato starch or sodium starch glycolate), and the like. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. (1975), incorporated herein by reference).

As used herein, the term "pharmaceutically acceptable salt" refers to any salt (e.g., obtained by reaction with an acid or a base) of a compound of the present invention that is physiologically tolerated in the target subject (e.g., a mammalian subject, and/or in vivo or ex vivo, cells, tissues, or organs). "Salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the terms "gene expression" and "expression" refer to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refer to regulation that increases and/or enhances the production of gene expression products (e.g., RNA or protein), while "down-regulation" or "repression" refer to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in Nucleic Acid Hybridization (1985)). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under "medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5×Denhardt's reagent (50×Denhardt's contains per 500 ml: 5 g Ficoll (Type 400, Pharamcia), 5 g BSA (Fraction V; Sigma)) and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk$^-$ cell lines, the CAD gene that is used in conjunction with CAD-deficient cells and the mammalian hypoxanthine-guanine phosphoribosyl transferase (hprt) gene that is used in conjunction with hprt$^-$ cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a problem with establishing and/or maintaining a pregnancy, a disease, illness, sickness, or disorder of bodily function. Test compounds comprise both known and potential therapeutic compounds. A test compound can be determined to be therapeutic by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

The term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "target RNA molecule" refers to an RNA molecule to which at least one strand of the short double-stranded region of an siRNA is homologous or complementary. Typically, when such homology or complementarity is about 100%, the siRNA is able to silence or inhibit expression of the target RNA molecule. Although it is believed that processed mRNA is a target of siRNA, the present invention is not limited to any particular hypothesis, and such hypotheses are not necessary to practice the present invention. Thus, it is contemplated that other RNA molecules may also be targets of siRNA. Such targets include unprocessed mRNA, ribosomal RNA, and viral RNA genomes.

DETAILED DESCRIPTION OF THE INVENTION

Selenium is a trace element involved in regulating aspects of the antioxidant defense mechanism in all living tissues by interacting with the body's glutathione (GSH) and its major Se-containing antioxidant enzymes, glutathione peroxidase (GPX) and thioredoxin reductase (See, e.g., Goehring et al., J. Anim. Sci. 59, 725-732 (1984); Gerloff et al., J. Anim. Sci. 70, 3934-3940 (1992)). Glutathione and GPX have the capacity to protect the integrity of unsaturated bonds of membrane phospholipids by extinguishing free radical attacks capable of initiating and propagating lipid oxidation (See, e.g., Meister and Anderson, Annu. Rev. Biochem. 52, 711-760 (1983); Deleve and Kaplowitz, Pharm. Ther. 52, 287-305 (1991); Palmer and Paulson, Nutr. Rev. 55, 353-361 (1997)).

Selenium has also been associated with reduced cancer risk in several epidemiologic studies (See, e.g., Salonen et al., Am. J. Epidemiol. 120: 342-349 (1984); Willett et al., Lancet 2: 130-134 (1983); Virtamo et al., Cancer 60: 145-148 (1987)). Various selenium compounds of natural and synthetic origin have been shown to inhibit tumor development in animal studies in a wide range of dosages (See, e.g., Ip, J. Nutr. 128: 1845-1854 (1998)). Although most animal studies have employed pharmacologic doses of selenium (>2 mg/kg) in cancer chemoprevention (See, e.g., Ip, J. Nutr. 128: 1845-1854 (1998)), selenium deficiency has also been shown to enhance mammary (See, e.g., Ip and Daniel, Cancer Res. 45: 61-65 (1985)) and UVB-induced skin carcinogenesis (See, e.g., Pence et al., 102: 759-761 (1994)).

Selenium is important for optimum fertility in males, in both humans and animals. For example, it has been shown that selenium supplementation of rooster diets significantly reduces the incidence of sperm abnormalities (See, e.g., Edens et al., Practical applications for selenomethionine: broiler breeder reproduction. In: *Nutritional Biotechnology in the Feed and Food Industries: Proceedings of Alltech's 18th Annual Symposium* (T. P. Lyons and K. A. Jacques, eds), Nottingham University Press, Nottingham, UK, pp. 29-42, 2002). Considerably less information is available on the effects of selenium in female fertility.

Selenium is ingested through the diet which can have a varying content of selenium. For example, in large parts of the world, crops with poor levels of selenium are cultivated because of low levels of selenium in the soil.

Multiple forms of selenium have been examined. These include inorganic selenium such as selenite, and organic sources, including selenium yeast. There is a significant difference between absorption and toxicity of inorganic and organic selenium, the inorganic compounds usually being absorbed and utilized less efficiently and also being more toxic than organic sources of selenium.

Multiple studies have attempted to reveal potential health benefits resulting from the ingestion of low levels of selenium. For example, low concentrations of an inorganic form of selenium, sodium selenate, have shown some potential health benefits (See, e.g., Furnsinn et al., Int. J. of Obesity and Related Metab. Dis., 19, 458-463 (1995)). However, at elevated dosage levels, beneficial effects are reversed and dangerous toxicity is manifested.

Research over the last two decades has suggested that selenium is effective in the reduction of cancer incidence when provided to animals at doses only 5- to 10-fold above nutritional requirement (See, e.g., El-Bayoumy, The role of selenium in cancer prevention, Philadelphia, Lippincott, 1-15, 1991). Chemoprevention studies with selenium in animal model systems have indicated that this element is effective for most, if not all of the organ systems and is protective against the carcinogenic effects of a wide variety of insults (See, e.g., El-Bayoumy, The role of selenium in cancer prevention, Philadelphia, Lippincott, 1-15, 1991). Both epidemiological studies and supplementation trials have also supported its efficacy in lowering the incidence of cancers of the liver, colon, prostate and lung (See, e.g., Yu et al. Biol Trace Elem Res, 56: 117-124 (1997); Clark et al., J Am Med Assoc, 276: 1957-1963 (1996); Yoshizawa et al., J Natl Cancer Inst, 90: 1219-1224, (1998); Brooks, et al., J Urol, 166: 2034-2038, (2001)). Other studies have demonstrated no beneficial effect for selenium reduction of cancers (See, e.g., Garland et al., J. Am. Coll Nutr., 12: 400-11 (1993); Ghadirian et al., Cancer Detect Prev, 24: 305-13 (2000)).

Heart disease has also been shown to be reduced in persons who consume certain amounts of selenium in their diet. The levels of selenium in the blood stream were correlated with the degree of progression of cardiovascular disease with those patients having the lowest levels of selenium having the most extensive coronary artery blockage Despite decades of research in the mechanisms of action of selenium, little to nothing is known regarding other potential targets of selenium (e.g., genes or regulatory pathways) and beneficial effects that might be provided to a subject through administration of selenium. Also lacking is information regarding what forms of selenium (e.g., organic, inorganic, or both) can and cannot be used for bringing about these effects. Thus, it would be of great value to elucidate various ways in which different forms of selenium could be used to benefit certain systems (e.g., nervous, endocrine, metabolic systems, etc.) of a subject (e.g., a human or non-human mammal, avain species, bovine or other animal). Furthermore, understanding how various forms of selenium differ in their ability to exert effects on a subject may provide the ability to customize treatments for subjects suffering from, or at risk of, a disease or disorder that might be benefited by such treatment (e.g., specific forms of selenium could be used independently or with other known agents to treat or prevent diseases or disorders). Identification of unwanted effects from the consumption of certain forms of selenium could may also be identified and avoided.

Accordingly, the present invention relates to compositions comprising selenium (e.g., organic selenium (e.g., selenized yeast (e.g., SEL-PLEX))) and methods of using the same (e.g., as a therapeutic and/or prophylactic treatment). For example, the present invention provides compositions comprising selenium (e.g., organic selenium (e.g., selenized yeast (e.g., SEL-PLEX))) and methods of using the same for treating and/or preventing one or more conditions (e.g., problems) disorders, and/or diseases related to establishing and/or maintaining a pregnancy. Compositions and methods of the present invention find use in, among other things, research and clinical (e.g., preventative and therapeutic) applications.

In some embodiments, the present invention provides a method for treating and/or preventing one or more events (e.g., problems (e.g., a condition, a disorder, and/or a disease)) related with establishing and/or maintaining a pregnancy in a female subject, comprising administrating to the subject a composition comprising selenium (e.g., organic selenium (e.g., selenized yeast (e.g., SEL-PLEX))) under conditions such that one or more genes associated with the establishment of and/or maintenance of pregnancy are altered (e.g., enhanced). The present invention identified a number of genes (e.g., the expression of which has been documented to be instrumental in the establishment and maintenance of pregnancy and/or healthy embryogenesis) that were upregulated in subjects after administration of selenium (e.g., organic selenium (e.g., selenized yeast (e.g., SEL-PLEX))) to the subjects compared to subjects that were not administered selenium (See Example 1). For example, these genes include, but are not limited to, TGF-β1, glutathione peroxidases, fibroblast growth factor 1 (FGF1), fibroblast growth factor 2 (FGF2), SNF1-like kinase, platelet-derived growth factor alpha (PDFGA), cyclin D1 (CCND1), activin A receptor type 1 (ACVR1), Sp3 transcription factor (SP3), homeobox A7, homeobox D12, retinoic acid receptor beta (RARB), insulin-like growth factor binding protein 7, Protein Kinase A, Serum and Glucocorticoid inducible-protein kinase (Sgk), and relaxin.

Relaxin is a 6 kDa protein hormone member of the insulin-like growth factor family (See, e.g. Shirota et al. Ann N Y Acad. Sci. 2005 May; 1041:144-6; Dschietzig and Stangl, 2003 Cell Mol Life Sci. 2003 April; 60(4):688-700). Relaxin exerts pronounced effects on the female reproductive tract (e.g., that are involved in the maintenance of pregnancy and successful parturition). Relaxin is important for normal delivery in several mammalian species because of its marked rearrangement of reproductive tract connective tissue. In rats, there is a major pre-labor surge in circulating relaxin levels and relaxin is critical for cervical dilation. In guinea pigs, relaxin significantly increases the intrapubic ligament to enlarge the diameter of the pubis. It is also essential for normal delivery in pigs. In humans, relaxin is involved in the establishment and maintenance of pregnancy and successful parturition. For example, relaxin stimulates production of several endometrial products including prolactin, glycodelin, insulin-like growth factor binding factor 1 (IGFBP-1) and vascular endothelial growth factor in progesterone-primed human endothelial cells in vitro. In rhesus monkeys, relaxin promotes uterine weight as well as endometrial lymphocyte and arteriole number. Overall, relaxin is viewed as a very significant factor in the establishment and/or maintenance of pregnancy (See, e.g., Goldsmith et al., 2004. Proceedings of the National Academy of Sciences, 101:4685-4689).

According to Brackett et al., (See, e.g., Bracket et al., 1997. General and Comparative Endocrinology, 105:155-163; Bracket et al., 1985. Biology of Reproduction, 32(Suppl. 1):43), at the time of onset of puberty or following molting in hens, a sevenfold increase in pubic bone width occurs. The widening of pubic bone width is analogous to the effect of relaxin on lengthening and widening of the pelvic girdle in other species (e.g., the guinea pig) during pregnancy (See, e.g. Zarrow, 1947. Proceedings of the Society for Experimental Biology and Medicine, 66:489-491). Thus, in hens, relaxin plays a role in oviposition by influencing biochemical as well as morphological alterations in the uterus, oviduct and pelvic ligaments. Furthermore, teachings regarding relaxin effects in hens are not limited to birds and/or animals. Indeed, the hen oviduct is viewed as one of the most valuable model systems for studying the general effects of sex hormones (e.g., estrogen and progesterone) as applied to all species (See, e.g., Dougherty and Sanders, 2005. Estrogen action: revitalization of the chick oviduct model. Trends in Endocrinology and Metabolism, 16:414-419).

Fibroblast growth factor 1 (FGF1) is involved in angiogenesis, cell proliferation and differentiation, embryonic development, organogenesis, and tissue repair, (See, e.g. Krauss et al., J Cell Sci. 2005 Jun. 1; 118(Pt 11):2355-62). Fibroblast growth factor 2 (FGF2) is involved in limb and nervous system development, cell cycle regulation, as well as muscle growth/differentiation (See, e.g., Poole et al. Dev Dyn. 2001 January; 220(1):1-17; Mehler, Results Probl Cell Differ. 2002; 39:27-52). SNF1-like kinase is involved in regulation of insulin receptor signaling, cell cycle regulation and muscle growth and differentiation (See, e.g., Stephenson et al., Genomics. 2004 June; 83(6): 1105-1). Platelet-derived growth factor alpha (PDFGA) is involved in growth factor activity, regulation of progression through the cell cycle, and cell proliferation (See, e.g., Betsholtz, Cytokine Growth Factor Rev. 2004 August; 15(4):215-28). Cyclin D1 is involved in cell cycle and cell division regulation (See, e.g., Nemer and Horb, Cell Cycle. 2007 January; 6(2):117-21). Activin A receptor type 1 (ACVR1) is involved in activin signaling, FSH production, and follicular development in the ovary (See, e.g., Florio et al., Steroids. 2003 November; 68(10-13): 801-7). Sp3 transcription factor (SP3) and homeobox (HOX) proteins (e.g., HOX A7 and HOX D12) are transcription factors involved in developmental processes (See, e.g., Koos et al. Ann N Y Acad. Sci. 2005 May; 1041:233-47; Li et al., Biochem Cell Biol. 2004 August; 82(4):460-71; Bondos, Sci STKE. 2006 Oct. 3; 2006(355):pe38; Hombria, Differentiation. 2003 October; 71(8):461-76; and DeLise, Osteoarthritis Cartilage. 2000 September; 8(5):309-34). Retinoic acid receptor beta (RARB) is involved in vertebrate development, steroid hormone receptor/retinoic acid receptor activity, as well as neural tube development in the embryo (See e.g., Mark et al., Annu Rev Pharmacol Toxicol. 2006; 46:451-80; Underhill et al., Novartis Found Symp. 2001; 232:171-85; discussion 185-8; and Jettan et al., Prog Nucleic Acid Res Mol. Biol. 2001; 69:205-47). Insulin-like growth factor binding protein 7 is involved with regulation of cell growth and insulin-like growth factor binding (See, e.g., Kleinberg et al., Endocrinology. 2007 March; 148(3):1080-8; Blum et al., J Clin Endocrinol Metab. 2007 January; 92(1):219-28).

Serum and Glucocorticoid inducible-protein kinase (Sgk) is an immediate-early gene known to be important in the proliferation and differentiation of granulosa cells surrounding the developing oocyte (See e.g., Alliston et al., 1997 Molecular Endocrinology, 11: 1934-1949; Chudgar et al., Mol. Vis. 2006 Sep. 30; 12:1117-26). Granulosa cells produce steroids and a range of other growth factors known to be essential for oocyte development (See, e.g., Wang et al., Fertil Steril. 2006 November; 86(5):1392-401; Machelon et al., J Gynecol Obstet Biol Reprod (Paris). 2006 September; 35(5 Pt 2):2S14-2S18).

Figure 5:
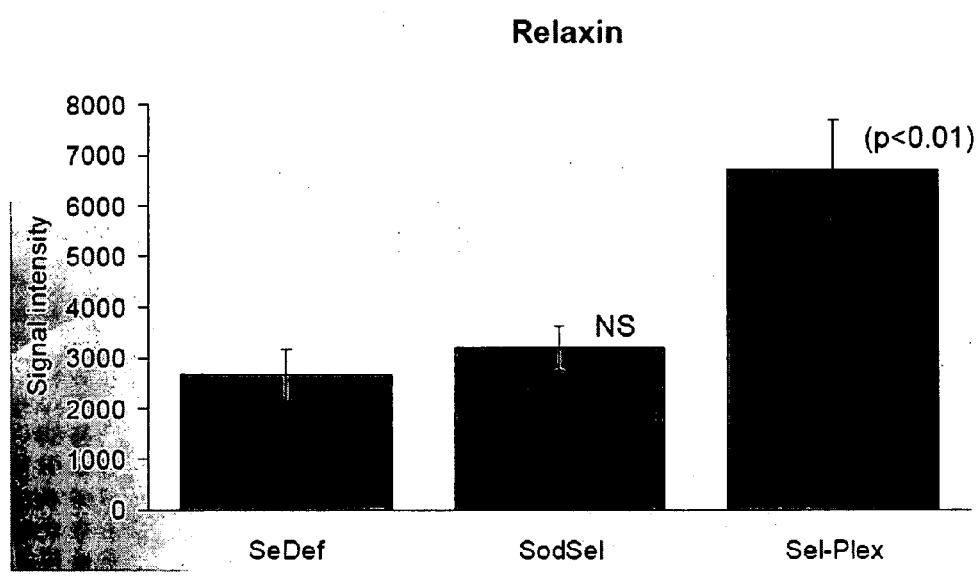
FIG. 5 shows the effect on relaxin gene expression in response to sodium selenite or SEL-PLEX administration.

Accordingly, in some embodiments, the present invention provides a method of enhancing the expression relaxin in a subject comprising providing a subject and a composition comprising selenium (e.g., organic selenium (e.g., selenized yeast (e.g., SEL-PLEX))) and administrating the composition to the subject under conditions such that the expression of relaxin is enhanced in the subject (e.g., compared to a subject not administered the composition) (See, e.g., Example 1 and FIG. 5).

In some embodiments, administration of selenium (e.g., organic selenium (e.g., selenized yeast (e.g., SEL-PLEX))) to a female subject (e.g., a subject that is, or that is attempting to become, pregnant) promotes fertilization and/or healthy embryogenesis and/or gestation in the subject (e.g., normal embryo development (e.g., limb and nervous system development, muscle growth and differentiation and neural tube development (e.g., due to the expression of one or more genes (e.g., fibroblast growth factor 2 (FGF2), SNF1-like kinase, platelet-derived growth factor alpha (PDFGA), cyclin D1 (CCND1), activin A receptor type 1 (ACVR1), Sp3 transcription factor (SP3), homeobox A7, homeobox D12, retinoic acid receptor beta (RARB), insulin-like growth factor binding protein 7, Protein Kinase A, Serum and Glucocorticoid inducible-protein kinase (Sgk), and/or relaxin (See FIG. 2) being altered (e.g., upregulated) upon administration of selenium))).

In some embodiments, fertilization and/or healthy embryogenesis and/or gestation in the subject (e.g., subsequent to administration of selenium (e.g., organic selenium (e.g., selenized yeast (e.g., SEL-PLEX))) results from proper rearrangement of connective tissues (e.g., within the uterus (e.g., of a human) and/or oviduct (e.g., in a hen)) during pregnancy. In some embodiments, fertilization and/or healthy embryogenesis and/or gestation in the subject (e.g., subsequent to administration of selenium (e.g., organic selenium (e.g., selenized yeast (e.g., SEL-PLEX))) results from correction of corpus luteum and/or placental insufficiency (e.g., due to the expression of genes induced subsequent to administration of selenium). In some embodiments, fertilization and/or healthy embryogenesis and/or gestation in the subject (e.g., subsequent to administration of selenium (e.g., organic selenium (e.g., selenized yeast (e.g., SEL-PLEX))) results from proper formation (e.g., widening) of the pubis. In some embodiments, fertilization and/or healthy embryogenesis and/or gestation in the subject (e.g., subsequent to administration of selenium (e.g., organic selenium (e.g., selenized yeast (e.g., SEL-PLEX))) results from increasing intrauterine fetal growth (e.g., due to induction of genes expression (e.g., within the female subject (e.g., within granulosa cells (e.g., that promote oocyte development)))). In some embodiments, genes induced by the granulosa cells are steroids and/or growth factors.

In some embodiments, fertilization and/or healthy embryogenesis and/or gestation in the subject (e.g., subsequent to administration of selenium (e.g., organic selenium (e.g., selenized yeast (e.g., SEL-PLEX))) results from proper generation and/or maintenance of endometrial products subsequent to administration of selenium. In some embodiments, fertilization and/or healthy embryogenesis and/or gestation in the subject (e.g., subsequent to administration of selenium (e.g., organic selenium (e.g., selenized yeast (e.g., SEL-PLEX))) results from proper formation and/or health of the oviduct, uterus and/or pelvic ligaments (e.g., in a hen administered selenium).

Accordingly, in some embodiments, because the present invention provides that the administration of selenium (e.g., organic selenium (e.g., selenized yeast (e.g., SEL-PLEX))) results in a significant elevation of expression of genes involved in the establishment of and/or maintenance of a pregnancy, the present invention identifies one or more classes of subjects that may benefit from administration of selenium (e.g., organic selenium (e.g., selenized yeast (e.g., SEL-PLEX))). For example, compositions (e.g., that enhance the expression of genes related to establishing and/or maintaining pregnancy when administered to a subject) and methods (e.g., of administering a composition comprising selenium to a subject) of the present invention may be utilized by any subject that is attempting to become or that is pregnant.

In some embodiments, compositions and methods of the present invention may be utilized (e.g., prescribed to and/or administered to) by a subject in which one or more of the following are desired: proper rearrangement of connective tissues (e.g., within the uterus (e.g., of a human) and/or oviduct (e.g., in a hen)) during pregnancy (e.g., related to increase expression of relaxin and/or other genes disclosed herein (e.g., the expression of which is altered by administration of selenium); correction of corpus luteum and/or placental insufficiency (e.g., due to the expression of genes induced subsequent to administration of selenium (e.g., relaxin and/or gsk); proper formation (e.g., widening) of the pubis (e.g., during pregnancy (e.g., related to the expression of relaxin); increased intrauterine fetal growth (e.g., due to induced expression of genes (e.g., within the female subject (e.g., within granulosa cells (e.g., that promote oocyte development (e.g., steroids and/or growth factors (e.g., those identified herein)))))))))); proper generation and/or maintenance of endometrial products; healthy embryogenesis and/or gestation (e.g., due to expression of one or more genes described herein (e.g., relaxin and/or gsk); and/or proper formation and/or health of the oviduct, uterus and/or pelvic ligaments (e.g., in a hen administered selenium (e.g., due to expression of relaxin and/or one or more other genes whose expression is upregulated subsequent to administration of selenium as described herein))).

In some embodiments, compositions and methods of the present invention may be utilized by (e.g., prescribed to and/or administered to) a subject identified (e.g., via a test and/or procedure (e.g., diagnostic test and/or procedure)) as one who will benefit from the compositions and methods of the present invention (e.g., identified as a subject at risk for having a problem with establishing and/or maintaining a pregnancy). For example, in some embodiments, prior to administrating compositions and methods of the present invention to a subject, a subject is first identified as one who has one or more of the following: placental insufficiency (See e.g., Lepercq and Mahieu-Caputo, 1998, Horm. Res. 49(suppl 2):14-19); a specific maternal weight and/or height prior to pregnancy (e.g., that is identified as being at risk for non full-term pregnancy); low weight gain during pregnancy; maternal history of non-full term pregnancies (e.g., spontaneous abortion, stillbirth, neonatal death, and/or premature parturition); previous offspring with low birth weight; specific maternal activities placing the pregnancy at risk (e.g., smoking, alcohol and/or drug use, and/or poor nutrition); early intrauterine infections; maternal medical diseases; multiparous pregnancies; a history of or newly experienced complications arising during pregnancy; and/or a general desire for establishing pregnancy and/or maintenance of a healthy pregnancy.

In some embodiments, a subject is identified (e.g., as a candidate for compositions and methods of the present invention) by measuring expression levels of certain genes (e.g., nucleic acid levels (e.g., cDNA, RNA, etc.) and/or proteins. For example, in some embodiments, the expression level of one or more genes associated with (e.g., important for) establishing pregnancy and/or maintaining pregnancy are measured in a subject, and a subject is identified as a candidate for receiving compositions and methods of the present invention. For example, in some embodiments, the expression level of one or more genes from the group fibroblast growth factor 2 (FGF2), SNF1-like kinase, platelet-derived growth factor alpha (PDFGA), cyclin D1 (CCND1), activin A receptor type 1 (ACVR1), Sp3 transcription factor (SP3), homeobox A7, homeobox D12, retinoic acid receptor beta (RARB), insulin-like growth factor binding protein 7, Protein Kinase A, Serum and Glucocorticoid inducible-protein kinase (Sgk), and relaxin are measured and subjects identified.

In some embodiments, a subject with low to non-detectable levels of one or more genes associated with (e.g., important for) establishing pregnancy and/or maintaining pregnancy (e.g., relaxin and/or sgk) compared to a normal, healthy control, and/or a to a level identified (e.g., through standardization) to be that of a subject likely to establish and/or maintain a healthy pregnancy, identified using the compositions and methods of the present invention, can be administered a composition comprising selenium (e.g., organic selenium (e.g., selenized yeast (e.g., SEL-PLEX))) in order to elevate expression of one or more of the genes with low to non-detectable expression levels. In some embodiments, at some point after administration (e.g., a point during administration (e.g., during a course of administration as described herein) or subsequent to the last administration), the expression level (e.g., nucleic acid and/or protein expression levels) of one or more of the genes can be monitored (e.g., detected (e.g., in order to characterize the effectiveness of the treatment)). In some embodiments, depending upon the expression level of the one or more genes, the administration of selenium may be altered (e.g., increased or decreased), terminated, or left unchanged. As described herein, the present invention is not limited by the method of detecting the expression of any particular protein and/or nucleic acid.

In some embodiments, a subject may begin utilizing compositions (e.g., comprising selenium (e.g., organic selenium (e.g., selenized yeast (e.g., SEL-PLEX)))) and methods of the present invention after any type of pregnancy related test, including, but not limited to, a test indicating that a subject is or is not pregnant (e.g., a blood or urine test (e.g., for human chorionic gonadotropin (hCG))), after any type of fetal screening test (e.g., tests used to identify and/or characterize certain traits or characteristics (e.g., tests performed to identify and/or characterize birth defects (e.g., amniocentesis, sonograms, nuchal translucency testing, and genetic screening (e.g., to identify and/or characterize down syndrome, spina bifida, cleft palate, Tay Sachs disease, sickle cell anemia, thalassemia, cystic fibrosis, or fragile×syndrome)))), a test indicating the size of a fetus (e.g., after use of morphometric and/or Doppler ultrasonic measurements to measure fetus size (e.g., size of head, limbs, etc.), a test indicating the size and/or formation and/or location of the uterus (e.g., use of morphometric and/or Doppler ultrasonic measurements to measure uterine size, location, formation, etc.), a test indicating multiple gestation, etc.). In some embodiments, a subject begins utilizing (e.g., administration of) compositions and methods of the present invention within 24 hours (e.g., within 18 hours, 9 hours, 6 hours, 3 hours, 1 hour or less) of such a pregnancy related test or after receiving the results of the same. In some embodiments, a subject begins administration of compositions and methods of the present invention within 1 week, within 3 days, within 2 days, or within 1 day of a pregnancy related test or after receiving the results of the same.

In some embodiments, a subject is identified as a candidate for the compositions and methods of the present invention because the subject displays low, non-normal gene and/or protein expression (e.g., of one or more genes and/or proteins) that correlates with poor fertility and/or poor fetal development and/or low birth weight. The present invention is not limited by the type of subject that may benefit from the compositions and methods described herein. Indeed, any subject with any problem related to establishing and/or maintaining pregnancy is contemplated to benefit from the compositions and methods disclosed herein. For example, in some embodiments, compositions and methods of the present invention are utilized by (e.g., prescribed to and/or administered to) a subject because the subject has been identified as one who has tried to become pregnant for more than six weeks, for more than two months, for more than 4 months, for more than 6 months, for more than a year, for more than two years, or for more than three years (e.g., without establishing a pregnancy).

In some embodiments, after a subject is identified as one that may benefit from the compositions and/or methods of the present invention, and is administered a composition of the present invention, and subsequently characterized for one or more beneficial results (e.g., alteration of gene expression involved with establishment of and/or maintenance of pregnancy) due to administration of a composition of the present invention, the subject may also be further classified and/or characterized post such characterization. For example, a subject may be characterized as one with high, medium or low probability of successful parturition and/or mature pregnancy (e.g., without additional help and/or medical intervention); or as a subject with a likelihood of complication resulting in non-full term gestation, miscarriage, etc. (e.g., without additional help and/or medical intervention).

In some embodiments, a subject administered and/or utilizing compositions and methods of the present invention may keep a record of one or more pieces of information throughout the treatment process. This information may include, but is not limited to, sleep habits, emotional status, temperature, eating habits, level of stress, and working habits.

The present invention provides that certain forms of selenium (e.g., organic selenium (e.g., selenized yeast (e.g., SEL-PLEX))) compared to other types of selenium (e.g., sodium selenite) are able to produce a significant elevation of expression of genes involved in the establishment of and/or maintenance of a pregnancy (e.g., relaxin). Thus, the present invention distinguishes between different forms of selenium that are useful and that are not useful in methods of the present invention (e.g., for enhancing expression of genes and/or proteins involved with establishing and/or maintenance of pregnancy).

For example, in some embodiments, the present invention provides a method of altering expression of one or more genes associated with establishment of and/or maintenance of pregnancy (e.g., relaxin, Sgk, etc.) in a subject comprising providing a subject; and a composition comprising a dried, non-viable selenium-enriched yeast (e.g., Sacchoromyces cerevisiae of accession number CNCM 1-3060, Collection Nationale De Cultures De Microorganismes (CNCM), Institut Pasteur, Paris, France (e.g., cultivated in a fed-batch fermentation that provides incremental amounts of cane molasses and selenium salts in a manner that minimizes the detrimental effects of selenium salts on the growth rate of the yeast and allows for optimal incorporation of inorganic selenium into cellular organic material with residual inorganic selenium being eliminated (e.g., using a rigorous washing process) and not exceeding 2% of the total selenium content)); and administering the composition to the subject under conditions such that the expression of one or more genes associated with establishment of and/or maintenance of pregnancy (e.g., relaxin, Sgk, etc.) is enhanced the subject (e.g., compared to a subject not administered the composition, or that is administered a different type of composition comprising selenium (e.g., sodium selenite)). In some embodiments, the one or more genes associated with establishment of and/or maintenance of pregnancy is relaxin. In some embodiments, enhancing expression of one or more genes associated with establishment of and/or maintenance of pregnancy (e.g., relaxin, Sgk, etc.) reduces and/or eliminates the risk of perinatal morbidity and/or mortality in the subject. In some embodiments, enhancing expression of one or more genes associated with establishment of and/or maintenance of pregnancy (e.g., relaxin, Sgk, etc.) increases fetal growth (e.g., fetal growth rate (e.g., due to nutrition, blood and/or oxygen supply, etc.) in the subject. In some embodiments, enhancing expression of one or more genes associated with establishment of and/or maintenance of pregnancy (e.g., relaxin, Sgk, etc.) increases the duration of gestation (e.g., into the second trimester, into the third trimester, and/or to full term). In some embodiments, enhancing expression of one or more genes associated with establishment of and/or maintenance of pregnancy (e.g., relaxin, Sgk, etc.) promotes the health of the uterus (e.g., promotes connective tissue formation and/or rearrangement). In some embodiments, enhancing expression of one or more genes associated with establishment of and/or maintenance of pregnancy (e.g., relaxin, Sgk, etc.) promotes the health of the embryo and/or fetus (e.g., promotes limb and nervous system development, muscle growth and differentiation, and/or neural tube development.). In some embodiments, enhancing expression of one or more genes associated with establishment of and/or maintenance of pregnancy (e.g., relaxin, Sgk, etc.) reduces the risk and/or incidence of spontaneous abortion, miscarriage, and/or birthing complications (e.g., of a human and/or non-human mammal, or of an avian species. In some embodiments, enhancing expression of one or more genes associated with establishment of and/or maintenance of pregnancy (e.g., relaxin, Sgk, etc.) promotes the health and development of hens and/or the hen's offspring.

In some embodiments, compositions and methods of the present invention are utilized in in vitro fertilization and/or embryo transfer settings. For example, in some embodiments, enhancing expression (e.g., in a subject administered a composition comprising selenium) of one or more genes associated with establishment of and/or maintenance of pregnancy (relaxin, Sgk, etc.) increases the likelihood of success for a successful pregnancy resulting from in vitro fertilization (IVF) and/or embryo transfer (ET) procedure. In some embodiments, a subject that is planning on undergoing an IVF or ET procedure (e.g., to benefit the health of the uterus and/or other supporting tissues important for pregnancy (e.g., in an aged (e.g., older than 20, older than 25, older than 30, older than 35, older than 40 years of age) female wishing to become pregnant) begins administration of a composition comprising selenium (e.g., organic selenium (e.g., selenized yeast (e.g., SEL-PLEX))) in advance of the procedure (e.g., 1 month ahead, 3 months ahead, six months ahead, 9 months ahead, 1 year ahead, or two years ahead). However, a subject that is planning on undergoing an IVF or ET procedure may also begin administration of a composition comprising selenium (e.g., organic selenium (e.g., selenized yeast (e.g., SEL-PLEX))) greater than two years or less than 1 month ahead of the procedure. In some embodiments, a subject who has an IVF or ET procedure performed is administered a composition of the present invention during the procedure and/or after the procedure.

In some embodiments, the present invention provides compositions and methods for the treatment, diagnosis and/or prevention of conditions (e.g., problems), disorders, and/or diseases involving fetal growth (e.g., including, but not limited to, intrauterine growth retardation and placental insufficiency). In some embodiments, the invention provides methods for modulating signaling pathways related to the polypeptide hormone, relaxin. In some embodiments, the present invention provides methods relating to the modulation of relaxin expression (e.g., nucleic acid and/or protein expression) and/or synthesis, relaxin receptor synthesis, relaxin binding to its receptor, and/or relaxin signaling (See, e.g., U.S. Patent Application Publication Nos. 20060247172 and 20010053553, each of which is hereby incorporated by reference in their entireties for all purposes).

In some embodiments, the present invention provides a method of increasing intrauterine fetal growth rate, comprising the step of administering to a pregnant subject a therapeutically effective amount of a composition comprising selenium (e.g., organic selenium (e.g., selenized yeast (e.g., SEL-PLEX))) for a time sufficient to increase the expression of one or more genes associate with fetal growth (e.g., relaxin (e.g., thereby increasing fetal growth rate)). In some embodiments, the composition comprising selenium (e.g., organic selenium (e.g., selenized yeast (e.g., SEL-PLEX))) is administered during the first, second, and/or third trimester of pregnancy. In some embodiments, the composition comprising selenium (e.g., organic selenium (e.g., selenized yeast (e.g., SEL-PLEX))) is administered for at least 2 weeks starting at ovulation. In yet another embodiment, the composition comprising selenium (e.g., organic selenium (e.g., selenized yeast (e.g., SEL-PLEX))) is administered before and after ovulation. In yet another embodiment, the composition comprising selenium (e.g., organic selenium (e.g., selenized yeast (e.g., SEL-PLEX))) is administered for about a week before ovulation and about four weeks after ovulation. The present invention is not limited to these particular time frames for administration of a composition comprising selenium (e.g., organic selenium (e.g., selenized yeast (e.g., SEL-PLEX))). Indeed, a composition comprising selenium may be administered months to years prior to any particular ovulation as well as one to 9 months or more after any particular ovulation.

In some embodiments, the present invention provides a method of increasing intrauterine fetal growth rate wherein a composition comprising selenium (e.g., organic selenium (e.g., selenized yeast (e.g., SEL-PLEX))) is administered in an amount sufficient to result in the birth of a baby of at least around normal birth weight. In some embodiments, the composition comprising selenium (e.g., organic selenium (e.g., selenized yeast (e.g., SEL-PLEX))) is administered in an amount sufficient to maintain a desired serum concentration of one or more gene products associated with establishing and/or maintaining a pregnancy described herein (e.g., relaxin) in the pregnant subject (e.g., of at least around 0.5-3.0 ng/mL (e.g., 0.1 ng/mL) although concentrations above 3.0 and below 0.5 ng/mL are also contemplated).

In some embodiments, the present invention provides a method of increasing intrauterine fetal growth rate comprising the step of administering to a pregnant subject a therapeutically effective amount of a composition comprising selenium (e.g., organic selenium (e.g., selenized yeast (e.g., SEL-PLEX))) for a time sufficient to increase fetal growth rate, wherein the increase in fetal growth rate is assessed by an imaging technique. The present invention is not limited by the type of imaging technique utilized. In some embodiments, the imaging technique is selected from a group comprising ultrasonic imaging and magnetic resonance imaging. In some embodiments, the subject (e.g., the imaged subject) is diagnosed and/or identified as hosting a fetus with intrauterine growth retardation (e.g., due to one or more of the conditions, diseases and/or disorders described herein). In some embodiments, diagnosing and/or identification of intrauterine growth retardation is obtained via use of an imaging technique (e.g., ultrasonic imaging or magnetic resonance imaging).

In some embodiments, the present invention provides a method of increasing intrauterine fetal growth rate comprising the step of administering to a pregnant subject a therapeutically effective amount of a composition comprising selenium (e.g., organic selenium (e.g., selenized yeast (e.g., SEL-PLEX))) wherein the subject has a condition, disease and/or disorder that increases the risk of fetal intrauterine growth retardation and/or low birth weight. The present invention is not limited by the type of condition, disease and/or disorder that may result in low birth weight and/or intrauterine growth retardation. Indeed, a variety of conditions, disorders and/or diseases are contemplated including, but not limited to, autoimmune disease (e.g., lupus), hyperthyroidism, hypertension, preeclampsia, infection, serum antiphospholipid antibodies, a history of spontaneous abortion or other non-full term pregnancy (e.g., miscarriage, stillbirth, premature parturition), a history of intrauterine growth retardation, a history of having children with low birth weight, a multiple-gestation pregnancy, and a pregnancy resulting from in vitro fertilization or embryo transfer.

The present invention is not limited by the subject treated with a composition comprising selenium (e.g., organic selenium (e.g., selenized yeast (e.g., SEL-PLEX))) of the present invention (e.g., for increasing the likelihood of successfully establishing and/or maintaining a healthy pregnancy in the subject (e.g., but enhancing expression of one or more genes involved in establishment and/or maintenance of pregnancy)). In some embodiments, the subject treated is a human. In some embodiments, the compositions and methods of the present invention may be used to treat pregnant human subjects or human subjects that desire to become pregnant. In some embodiments, the compositions and methods may be used to treat non-human mammals (e.g., a horse, cow, sheep, goat, swine, deer, dog, cat, rat, and/or a mouse (e.g., that are pregnant or that are desired to become pregnant)). In some embodiments, the subject treated is from an avian species (e.g., domesticated fowl (e.g., chickens, turkeys, ducks, geese, and guinea fowl, etc.) and other game birds (e.g., quail, pheasants, grouse, partridges, emu, ostriches, pigeons, etc.). In some embodiments, the compositions and methods of the present invention may be used to treat (e.g., administered to) aquatic species (e.g., fresh water and marine (salt water) species (e.g., including, but not limited to, fish (e.g., bass, catfish, carp, cod, crappie, eel, flounder, grouper, haddock, halibut, herring, kingfish, mackerel, mahi mahi, orange roughy, perch, pike, Pollock, salmon, sardine, shark, snapper, sole, tilapia, trout, tuna, and walleye), crustaceans (e.g., crab, crayfish, lobster, prawn, and shrimp), mollusks, etc.).

In some embodiments, the present invention provides a method of reducing the risk or incidence of spontaneous abortion in a pregnant subject, the method comprising administering to the pregnant subject an amount of a composition comprising selenium (e.g., organic selenium (e.g., selenized yeast (e.g., SEL-PLEX))) effective to reduce the risk or incidence of spontaneous abortion. In some embodiments, the composition comprising selenium (e.g., organic selenium (e.g., selenized yeast (e.g., SEL-PLEX))) is administered during and/or prior to the first trimester of pregnancy. In some embodiments, the composition comprising selenium (e.g., organic selenium (e.g., selenized yeast (e.g., SEL-PLEX))) is administered during the first, second, and/or third trimester of pregnancy.

In some embodiments, compositions and/or methods of the present invention are utilized in conjunction with monitoring of patients undergoing clinical evaluation for treatment of fetal growth abnormalities, infertility, and/or one or more complications related to pregnancy. In some embodiments, such methods also include monitoring of the size of a fetus with respect to its gestational age.

Thus, in some embodiments, compositions and methods described herein may be performed in conjunction with, prior to, or subsequent to one or more techniques for measuring fetal size and/or growth. For example, upon identifying a subject (e.g., human) exhibiting higher or lower levels of one or more genes involved in the establishment and/or maintenance of pregnancy (e.g., relaxin (e.g., in serum)) relative to that of a corresponding control subject, the size and/or growth rate of one or a plurality of fetuses carried by the subject can be measured to further clarify whether the one or plurality of fetuses exhibit abnormal growth. In some embodiments, compositions and methods described herein may be used in combination (e.g., concurrently) with diagnostic techniques to identify abnormal fetal growth. In some embodiments, a diagnosis involves an assessment the size and/or gestational age of the fetus. For example, an early ultrasonographic examination can be used to determine the gestational age (See, e.g., Benson and Doubilet, 1991, AJR Am. J. Roentgenol. 157:1275-1277). Other imaging techniques, such as magnetic resonance imaging, can also be used to estimate gestational age and/or to monitor intrauterine growth of the fetus as well as growth of the placenta. In the absence of an accurate estimate of gestational age, serial measurements of fetal size may be used to assess whether or not fetal size is appropriate. In some embodiments, an analysis utilizing morphometric and/or Doppler ultrasonic measurements may be used to identify abdominal circumference and estimated fetal weight (e.g., based on measurements of head size, abdominal size and femur length (e.g., to identify fetuses likely to be large or small for their gestational age (See, e.g., Chang et al., 1992, Obstet. Gynecol. 80:1030-8)).

The present invention is not limited by any particular method of detecting the expression (e.g., nucleic acid and/or protein expression) of one or more genes related to the establishment and/or maintenance of pregnancy in a subject (e.g., prior to, during and/or after administration of a composition of the present invention). In some embodiments, the detection of one or more genes (e.g., wild type and/or variant forms thereof (e.g., polymorphic and/or mutant forms) related to the establishment and/or maintenance of pregnancy in a subject involves, for example, their amplification (e.g., by PCR (e.g., that may be followed by the detection of the amplified molecules using techniques well known to those of skill in the art)). Methods of detecting wild type and variant forms of genes, as well as detecting gene products (e.g. using antibodies), are well known to those of skill in the art (e.g., for exemplary methods of detecting wild type and mutant forms of relaxin, and relaxin gene products, See, U.S. Patent Publication No. 20060247172, hereby incorporated by reference in its entirety).

In some embodiments, the present invention demonstrates how specific forms of selenium (e.g., organic selenium, (e.g., selenized-yeast (e.g., SEL-PLEX))) may be used to benefit a subject. In particular, the present invention provides that compositions and methods of the present invention can be used to stabilize or increase the general health of a developing embryo, fetus, and/or uterus within a female subject. For example, as described in detail herein, the present invention provides compositions and methods that can enhance expression of genes and/or proteins that are important in the establishment and/or maintenance of pregnancy (e.g., a full term and/or healthy pregnancy).

In some embodiments, the present invention also provides that a composition comprising selenium (e.g., organic selenium, (e.g., selenized-yeast (e.g., SEL-PLEX))) may be used in combination (e.g., co-administered with) other agents that promote the establishment and/or maintenance of pregnancy (e.g., a full term and/or healthy pregnancy). One or ordinary skill in the art knows well that there a number of such agents currently available. Examples of such agents include, but are not limited to, agents utilized in IVF and/or embryo transfer procedures (e.g., urofollitropin, follitropin alpha and follitropin beta, chorionic gonadotropins, Clomiphene citrate, gonadorelin, leuprolide, menotropins, estrogen, prolactin, testosterone, progesterone), agents utilized to promote the health of the embryo, fetus, and/or mother (e.g., vitamins, minerals, hormones, etc.). Thus, in some embodiments, the present invention provides one or more forms of selenium (e.g., SEL-PLEX) that is biologically available and is administered alone or co-administered with an agent used for promoting the establishment and/or maintenance of pregnancy (e.g., a full term and/or healthy pregnancy).

In some embodiments, the form of selenium administered to a subject will depend on the target (e.g., gene) sought to be treated. As demonstrated by the present invention, the presence and level of beneficial effect attained varies depending on the form of selenium used (See Examples 1). In preferred embodiments, selenium is provided in the form of SEL-PLEX. In other embodiments, selenium is provided as sodium-selenite. In still other embodiments, selenium is provided as selenomethionine or selenium enriched yeast. In some embodiments, selenium is provided as selenocysteine or a selenate compound. In some embodiments, selenium may be chemically linked to an agent (e.g., an agent used for promoting ovulation) to form a selenium-agent derivative.

Once the desired form of selenium is chosen, it can be administered alone or in combination with one or more agents used for promoting the establishment and/or maintenance of pregnancy (e.g., a full term and/or healthy pregnancy). The agent may be one approved by a regulatory authority for such a treatment (e.g., the US Food and Drug Administration (FDA) or the European Medicines Evaluation Agency (EMEA)).

The present invention is not limited by the composition and/or formulation comprising selenium. Nutritional selenium levels have been established by the FDA (See 21 C.F.R. 101.9(c)(8)(iv), January 1994). Humans and animals can safely metabolize limited amounts of both inorganic and organic forms of selenium and can convert non-methylated selenium to mono-ordi-or trimethylated derivatives, of which the monomethylated derivatives are most toxic. (See, e.g., Bedwal, R. S., et al., Medical Hypotheses, 41 (2):150-159 (August 1993)). The FDA has adopted Reference Daily Intakes (RDIs) of 70 micrograms for selenium. Selenium dosage of 600 micrograms per day has been reported as safe. (See, e.g., Ferris G. M. Lloyd, et al., App. Clin. Biochem., 26:83-88 (1989)). At about this dosage, normal activity of the enzyme glutathione reductase safely converts selenogluthatione to hydrogen selenide in the liver and erythrocytes and is ultimately excreted. Thus, at such lower dosages, the body is able to safely metabolize and excrete selenium that is present in a free metallic form. However, as with many trace elements (e.g., selenium), at higher dosage levels or concentrations the beneficial effects are reversed and dangerous toxicity is manifested. (See, e.g., Furnsinn, C. et al., Internat'l J. of Obesity and Related Metab. Dis., 19(7):458-463 (1995)).

Therefore, the administration of selenium in the natural form involves a scientific and medical trade-off because, when administered in relatively low concentrations, selenium provides beneficial health effects, however, at higher concentrations, selenium exhibits dramatic toxicity such that the potential health benefits are lost and toxicity becomes the primary concern.

As described above, the present invention demonstrates that certain forms of selenium (e.g., SEL-PLEX) are capable of providing beneficial effects to a subject that other forms of selenium (e.g., selenomethionine) do not. The present invention contemplates the use of multiple forms of selenium. The source of selenium may be a synthetic or natural source, and the selenium may be organic or inorganic. Evidence has shown that organic forms of selenium (e.g., selenomethionine and selenium enriched yeast) may be less toxic and better absorbed than inorganic forms (See, e.g., Mahan, Proceedings of the 15th Annual Symposium Nottingham University Press, Nottingham, UK, pp. 523-535 (1999)). As described herein, and depending on the target sought to be treated in a subject (e.g., gene expression involved in promoting the establishment and/or maintenance of pregnancy (e.g., a full term and/or healthy pregnancy)), multiple forms of selenium may be used independently or in combination with one another. Natural sources of selenium include, but are not limited to, selenium enriched (e.g., selenized) yeast. The yeast strain used is not limiting.

In certain preferred embodiments of the present invention, SEL-PLEX (Alltech, Lexington, Ky.) is the selenium form of choice for formulations and compositions. In some embodiments, compositions comprising SEL-PLEX provide a more biologically available form of selenium compared to other forms of selenium. However, other forms of selenium may also find use in the present invention including derivative or modifications of SEL-PLEX or other forms of selenium enriched yeast, selenomethionine, selenocysteine, a selenite compound, a selenate compound, or derivatives, salts, or modifications thereof. Thus, in some embodiments, each of these forms of selenium may be used as a component of a formulation. Alternatively, each of the above described forms of selenium may be linked (e.g., chemically or physically) to a drug or therapeutic to form a selenium-drug derivative. Additionally, compositions and formulations are not limited to one form or selenium. Indeed, a composition or formulation may comprise multiple forms of selenium (e.g., SEL-PLEX and Sod-sel).

Other forms of selenium that find use in various embodiments of the present invention are described in U.S. Pat. Nos. 6,911,550, 6,197,295, 5,221,545, and 6,576,233, and U.S. Pat. App. Nos. 20010043925, 20050069594, and 20050089530, herein incorporated by reference in their entireties.

Accordingly, the present invention provides pharmaceutical compositions which may comprise one or more forms of selenium, alone or in combination with at least one other agent, such as a stabilizing compound, and may be administered in any sterile, biocompatible pharmaceutical carrier, including, but not limited to, saline, buffered saline, dextrose, and water.

Selenium (e.g., SEL-PLEX) can be administered to a subject (e.g., a patient) by a variety of means including, but not limited to, via pill or tablet form and/or intravenously in a pharmaceutically acceptable carrier such as physiological saline. Standard methods for intracellular delivery of compounds can be used (e.g., delivery via liposome). Such methods are well known to those of ordinary skill in the art. Formulations also contemplated in the present invention include those useful for parenteral administration, such as intravenous, subcutaneous, intramuscular, and intraperitoneal.

As is well known in the medical arts, dosages for any one subject may depend upon many factors, including the patient's size, body surface area, age, the particular compound to be administered, sex, time and route of administration, general health, and interaction with other drugs being concurrently administered.

Accordingly, in some embodiments of the present invention, compositions and/or formulations comprising selenium can be administered to a subject alone, or in combination with other forms of selenium, drugs, small molecules, or in pharmaceutical compositions where it is mixed with excipient(s) or other pharmaceutically acceptable carriers. In one embodiment of the present invention, the pharmaceutically acceptable carrier is pharmaceutically inert. In another embodiment of the present invention, compositions comprising selenium may be administered alone to subjects (e.g., that is pregnant or that desires to become pregnant). Compositions comprising selenium (e.g., SEL-PLEX alone or in combination with one or more other forms of selenium) may be added to a nutritional drink or food (e.g., ENSURE, POWERBAR, or the like), a multi-vitamin, nutritional products, food products, etc. for daily consumption.

Depending on the target sought to be altered by treatment (e.g., gene expression associated with establishing and/or maintaining pregnancy), these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of the pharmaceutical agent may be that amount that alters the expression of a specific gene (e.g., relaxin and/or gsk). Determination of effective amounts is well within the capability of those skilled in the art, especially in light of the disclosure provided herein.

In addition to the active ingredients these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations which can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For compositions or formulations comprising selenium, conditions indicated on the label may include treatment of condition related to prophylactic or therapeutic treatment of neurodegenerative disease or cognitive function.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

For any compound used in the methods of the invention, the therapeutically effective dose can be estimated initially from cell culture assays. Then, preferably, dosage can be formulated in animal models (particularly murine models) to achieve a desirable circulating concentration range.

A therapeutically effective dose, in the context of establishing and/or maintaining pregnancy, is an amount necessary to improve the likelihood of establishing and/or maintaining pregnancy (e.g., from embryonic to fetal state, or from first to second trimester, or from second to third trimester, etc.). In some embodiments, an effective amount is sufficient to achieve a successful result in at least 55%, at least 65%, at least 75%, at least 85%, or at least 95% of the occasions administered (e.g., in the absence of other factors). An effective amount can be administered in one or more administrations, applications or dosages and is not intended to be limited to a particular formulation or administration route.

Toxicity and therapeutic efficacy of compositions of the present invention can be determined by standard pharmaceutical procedures in cell cultures or experimental animals (e.g., for determining the $LD_{50}$ (the dose lethal to 50% of the population) and the $ED_{50}$ (the dose therapeutically effective in 50% of the population)). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage may be chosen by a subject or by a physician in view of the patient to be treated. Dosage and administration are adjusted to provide sufficient levels of the active moiety or to maintain the desired effect (e.g., alteration of gene expression in a subject). Additional factors that may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

In some embodiments, selenium (e.g., organic selenium (e.g., selenized yeast (e.g., SEL-PLEX))) is administered at a daily dose of between 25 and 800 µg per day (e.g., SEL-PLEX is administered to a subject in such a way so as to provide between 25 and 800 µg of selenium to the subject each day). In preferred embodiments, the selenium (e.g., organic selenium (e.g., selenized yeast (e.g., SEL-PLEX))) is administered at a daily dose of between 200 and 500 µg per day. In other preferred embodiments, selenium is administered at a daily dose of between 200 and 400 µg per day. Doses outside of 25 and 800 µg may be used. In some embodiments, a single dose of selenium (e.g., organic selenium (e.g., selenized yeast (e.g., SEL-PLEX))) is administered once daily. In other embodiments, 2, 3, 4, or more doses may be administered each day (e.g., once in the morning and once at night, or once every 4 to 6 hours). For example, in some embodiments, selenium is administered to a subject in three separate, more than three separate, two separate, or less than two separate doses. In some preferred embodiments, the daily dose is administered in a time release capsule. In some preferred embodiments, the daily dose is between 25-75 µg of selenium. In other preferred embodiments, the daily dose is 200 µg of selenium (e.g., organic selenium (e.g., selenized yeast (e.g., SEL-PLEX))).

The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Compositions and formulations comprising selenium are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Thus, in some embodiments, pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

Thus, in some embodiments, the compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

In some embodiments, the invention provide pharmaceutical compositions containing (a) one or more forms of selenium (e.g., SEL-PLEX and/or Sod-sel) and (b) one or more other agents (e.g., a hormone utilized for IVF procedure). In some embodiments, two or more combined agents may be used together or sequentially.

The present invention also includes methods involving co-administration of compounds comprising selenium described herein with one or more additional active agents (e.g., a hormone utilized for IVF procedure). Indeed, it is a further aspect of this invention to provide methods for enhancing prior art therapies and/or pharmaceutical compositions by co-administering a composition comprising selenium of this invention. In co-administration procedures, the agents may be administered concurrently or sequentially. In one embodiment, the compounds described herein are administered prior to the other active agent(s). The pharmaceutical formulations and modes of administration may be any of those described above. In addition, the two or more co-administered agents may each be administered using different modes or different formulations. The additional agent(s) to be co-administered (e.g., a hormone utilized for IVF procedure) can be any of the well-known agents in the art, including, but not limited to, those that are currently in clinical use.

Treatment of the various conditions, diseases and/or disorders described herein are often generally limited by the following two major factors: (1) the development of drug resistance and (2) the toxicity of known therapeutic agents. Some therapeutic agents have deleterious side effects, including non-specific lymphotoxicity and renal toxicity.

The methods described herein address both these problems. Drug resistance, where increasing dosages are required to achieve therapeutic benefit, is overcome by co-administering the compounds comprising selenium described herein with the known agent. In some embodiments, the compounds described herein sensitize target cells to known agents (and vice versa) and, accordingly, less of these agents are needed to achieve a therapeutic benefit.

The sensitizing function of the claimed compounds also addresses the problems associated with toxic effects of known therapeutics. In instances where the known agent is toxic, it is desirable to limit the dosages administered in all cases, and particularly in those cases were drug resistance has increased the requisite dosage. Thus, in some embodiments, when the claimed compounds are co-administered with the known agent, they reduce the dosage required which, in turn, reduces the deleterious effects. Further, because the claimed compounds are themselves both effective and non-toxic in moderate doses, co-administration of proportionally more of these compounds than known toxic therapeutics will achieve the desired effects while minimizing toxic effects.

It is contemplated that the compositions and methods of the present invention will find use in various settings, including research and clinical diagnostics and therapeutics. For example, compositions and methods of the present invention also find use in studies of embryogenesis, fetal development, and birthing (e.g., of human and non-human mammal subjects, as well as avian species). Thus, uses of the compositions and methods provided by the present invention encompass human and non-human subjects and samples from those subjects, and also encompass research as well as diagnostic applications. Thus, it is not intended that the present invention be limited to any particular subject and/or application setting.

EXPERIMENTAL

The following examples are provided in order to demonstrate and further illustrate certain preferred embodiments and aspects of the present invention and are not to be construed as limiting the scope thereof.

Example 1

Administration of Selenium Enhances Reproduction Potential

In an effort to examine possible benefits of administration of selenium on female reproductive performance, hens were randomly selected from a broiler-breeder flock housed at Coldstream poultry facility, University of Kentucky. The hens were maintained on a selenium-deficient diet from 6 weeks of age until 22 weeks of age and were then placed on the following dietary treatments for over forty weeks until the time of sampling: 1) Control, selenium-deficient, Torula yeast-based diet (0.02 ppm selenium); 2) The control diet supplemented with 0.3 ppm selenium from sodium selenite; and 3) The control diet supplemented with 0.3 ppm selenium from SEL-PLEX. Hens were taken from each of the three experimental groups, their oviducts removed, flash-frozen and stored at −80° C. prior to RNA isolation.

Labeled RNA preparations from oviduct were hybridized with AFFYMETRIX chicken genome arrays containing 38,000 probe sets using standard methodology. Overall, it was found that 5,105 transcripts were significantly affected by at least one selenium treatment in hen oviduct.

Dietary selenium supplementation increased the expression levels of classical selenium-associated genes. For example, as described herein, selenium is known for its role in antioxidant systems, mainly because selenium (as selenocysteine) is a key component of glutathione peroxidases (GSH-Px). These are a class of enzymes that detoxify hydrogen peroxides and lipid hydroperoxides. Thus, glutathione peroxidases are believed to function to protect a cell against reactive oxygen species (ROS) produced as byproducts of aerobic cellular metabolism.

For example, the fold change (FC) in the expression of two Glutathione Peroxidases (GSH-PX) genes in oviduct (relative to selenium deficient hens) induced by sodium selenite (SS) and Sel-Plex (SP) are shown in FIG. 1. Significant induction of both Glutathione Peroxidases analyzed was noted for hens administered selenium in the form of SEL-PLEX, whereas significant induction of only Glutathione Peroxidase 3 was noted for administration of selenium in the form of sodium selenite. Administration of selenium to the hens also resulted in the up-regulation of genes encoding a variety of selenoproteins, including Selenoprotein P, Selenoprotein T, Selenoprotein 15 kDa and Selenoprotein K.

Administration of selenium to hens also resulted in a heretofore undocumented alteration of expression of genes involved with the establishment of and/or maintenance of pregnancy (e.g., genes encoding transcription and growth factors in hen oviduct). For example, overall changes in the expression profiles of genes associated with establishing and/or maintaining pregnancy in response to sodium selenite or Sel-Plex are shown in FIGS. 2 and 3. The numbers indicate Fold Change (FC) relative to selenium deficiency, the grey background indicates a statistically significant up-regulation ($p<0.05$) and the black background no significant change relative to selenium deficiency. The biological processes in which these growth and transcription factors are involved in are briefly described and generally relate to factors that are involved in key areas of reproduction and embryogenesis (e.g., including, but not limited to follicular development in ovary, and embryonic limb and nervous system development, muscle growth and differentiation and neural tube development).

Figure 4:
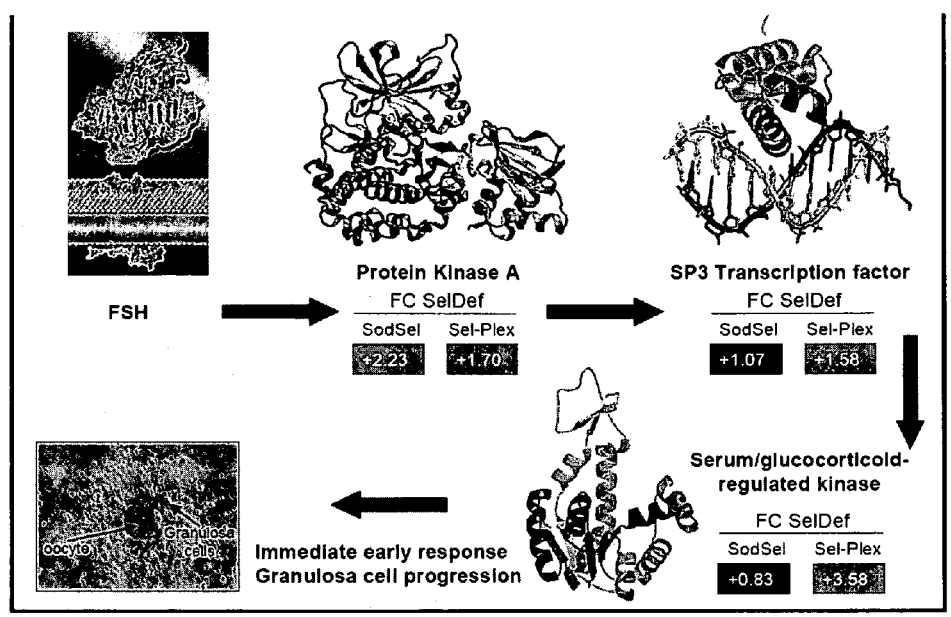
FIG. 4 shows the changes in expression profiles of Protein Kinase A, transcription factor SP3 and Serum/glucocorticoid-regulated kinase (Sgk), and an interrelation among the same, in response to sodium selenite or SEL-PLEX administration. The numbers indicate Fold Change (FC) relative to selenium deficiency.

Additionally, a number of linked effects were also observed that have not previously been associated with administration of selenium that also have the ability to alter (e.g., enhance) fertility and oocyte development. For example, follicle stimulating hormone (FSH) activates protein kinase A, which in turn activates the transcription factors SP1 or SP3. These transcription factors can activate serum and glucocorticoid inducible-protein kinase, sgk. Sgk is an immediate-early gene known to be important in the proliferation and differentiation of granulosa cells surrounding the developing oocyte (See, e.g., Alliston et al., 1997. Molecular Endocrinology, 11: 1934-1949). Granulosa cells produce steroids and a range of other growth factors known to be essential for oocyte development. In the case of hens administered selenium relative to selenium-deficient hens, up-regulation of the genes encoding protein kinase A, SP3 and Sgk, the interrelation among them, and their potential biological effects are shown in FIG. 4. Administration of SEL-PLEX to the hens led to significant elevation of expression of Protein Kinase A, SP3 and Sgk, whereas administration of sodium selenite did not induce significant expression of SP3 or Sgk.

Another striking and unexpected effect of administration of selenium was observed with the gene encoding the hormone relaxin. Relaxin is a 6 kDa protein hormone member of the insulin-like growth factor family (See, e.g., Shirota et al., Ann N Y Acad. Sci. 2005 May; 1041:144-6; Dschietzig and Stangl, 2003 Cell Mol Life Sci. 2003 April; 60(4):688-700). In many mammalian species, relaxin exerts pronounced effects on the female reproductive tract that are involved in the maintenance of pregnancy and successful parturition. Relaxin is important for normal delivery in several mammalian species because of its marked rearrangement of reproductive tract connective tissue. In rats, there is a major prelabor surge in circulating relaxin levels and relaxin is critical for cervical dilation. In guinea pigs, relaxin significantly increases the intrapubic ligament to enlarge the diameter of the pubis. It is also essential for normal delivery in pigs. In humans, relaxin stimulates production of several endometrial products including prolactin, glycodelin, insulin-like growth factor binding factor 1 (IGFBP-1) and vascular endothelial growth factor in progesterone-primed human endothelial cells in vitro. In rhesus monkeys, relaxin stimulated uterine weight as well as endometrial lymphocyte and arteriole number. Overall, relaxin is viewed as a very significant factor in the establishment and/or maintenance of pregnancy (See, e.g., Goldsmith et al., 2004. Proceedings of the National Academy of Sciences, 101:4685-4689).

According to Brackett et al., (See, e.g., Bracket et al., 1997. General and Comparative Endocrinology, 105:155-163; Bracket et al., 1985. Biology of Reproduction, 32(Suppl. 1):43), at the time of onset of puberty or following molting, a sevenfold increase in pubic bone width occurs. The widening of pubic bone width is analogous to the effect of relaxin on lengthening and widening of the pelvic girdle in the guinea pig during pregnancy (See, e.g., Zarrow, 1947. Proceedings of the Society for Experimental Biology and Medicine, 66:489-491). Thus, in hens, relaxin may assisting in oviposition by influencing biochemical as well as morphological alterations in the uterus, oviduct and pelvic ligaments.

Thus, the ability to alter (e.g., increase) relaxin levels in various subjects therefore may exist as one means of improving reproductive function in the host subject (e.g., human or non-human animal, avian species, etc.) This is particularly true when it is considered that hen oviduct is viewed as one of the most valuable model systems for studying the general effects of sex hormones, such as estrogen and progesterone as applied to all species (See, e.g., Dougherty and Sanders, 2005. Estrogen action: revitalization of the chick oviduct model. Trends in Endocrinology and Metabolism, 16:414-419).

When subjects were administered selenium, the gene encoding relaxin was significantly upregulated (e.g., 2.52-fold) by SEL-PLEX (p=0.0033) relative to selenium deficient animals, whereas sodium selenite had no significant effect on relaxin gene expression levels (See FIG. 5). Accordingly, the present invention provides a method of enhancing the expression relaxin in a subject comprising providing a subject and a composition comprising selenium (e.g., organic selenium (e.g., selenized yeast (e.g., SEL-PLEX))) and administrating the composition to the subject under conditions such that the expression of relaxin is enhanced in the subject (e.g., compared to a subject not administered the composition).

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

The invention claimed is:

1. A method of treating a female subject that is pregnant or attempting to become pregnant comprising:
   a) identifying a female subject that will benefit from the treatment, comprising measuring a level of relaxin gene or gene product expression in said female subject, and identifying the female subject by determining whether the level of expression of relaxin gene or gene product is lower than a normal healthy control female subject, and
   b) administering an effective amount of a composition comprising a dried, nonviable selenium-enriched yeast to said female subject to enhance-relaxin gene or gene product expression compared to a control female subject not administered said composition, wherein the total selenium content of said yeast comprises two percent or less inorganic selenium.

2. The method of claim 1, wherein measuring relaxin gene or gene product expression comprises detecting nucleic acid expression and/or protein expression.

3. The method of claim 1, wherein said method further comprises: c) measuring relaxin gene or gene product expression in said female subject after administration of said composition.

4. The method of claim 1, wherein the female subject is identified as a subject selected from the group consisting of: a subject desiring reduction and/or elimination of the risk of perinatal morbidity and/or mortality; a subject desiring an increase in fetal growth in the subject; a subject desiring an increase in the duration of gestation in said subject; a subject desiring the promotion of connective tissue formation and/or rearrangement in the subject; a subject desiring promotion of proper formation of the pubis; a subject desiring a reduction in the risk and/or incidence of spontaneous abortion; a subject desiring a reduction in the risk and/or incidence of miscarriage; a subject desiring a reduction in the risk and/or incidence of stillbirth; and a subject desiring a reduction in the risk and/or incidence of birthing complications.

5. The method of claim 1, wherein measuring relaxin gene expression comprises use of a nucleic acid probe.

6. A method of treating a female subject that is pregnant or attempting to become pregnant comprising:
   a) identifying a female subject that will benefit from the treatment, wherein identifying comprises measuring the level of relaxin gene or gene product expression in said female subject, and identifying the female subject by determining whether the level of expression of relaxin gene or gene product is lower than a normal healthy control female subject; and
   b) administering an effective amount of a composition comprising a dried, nonviable selenium-enriched yeast to said female subject to enhance a level of relaxin gene or gene product expression compared to a control subject not administered said composition, wherein the total selenium content of said yeast comprises two percent or less inorganic selenium;
   c) measuring the level of relaxin gene or gene product expression in said female subject after administration of said composition; and
   d) utilizing said level of relaxin gene or gene product expression after administration of said composition to determine a course of treatment selected from the group consisting of increasing the amount of said composition administered to said female subject, decreasing the amount of said composition administered to said female subject and terminating administration of said composition to said female subject.

7. The method of claim 6, wherein relaxin gene product is relaxin protein.

* * * * *